United States Patent [19]
Kass

[11] Patent Number: 5,830,153
[45] Date of Patent: Nov. 3, 1998

[54] CONTROLLED SURGICAL CORE BIOPSY SYSTEM

[76] Inventor: Erik S. Kass, 20 Chapel St., Apt. #312A, Brookline, Mass. 02146

[21] Appl. No.: 707,553

[22] Filed: Sep. 4, 1996

Related U.S. Application Data

[62] Division of Ser. No. 233,470, Apr. 26, 1994, Pat. No. 5,570,699.

[51] Int. Cl.⁶ ........................................... A61B 5/00
[52] U.S. Cl. ............................................. 600/567
[58] Field of Search ............................ 128/749, 751–754; 606/167, 170; 600/562, 564–567

[56] References Cited

U.S. PATENT DOCUMENTS

| | | | |
|---|---|---|---|
| 2,710,000 | 6/1955 | Cromer et al. | 128/754 |
| 4,461,305 | 7/1984 | Cibley | 128/754 |

FOREIGN PATENT DOCUMENTS

| | | | |
|---|---|---|---|
| 3909575 | 8/1990 | Germany | 128/754 |
| 483829 | 2/1970 | Switzerland | 128/754 |
| 0683726 | 9/1979 | U.S.S.R. | 128/754 |
| 1178422 | 9/1985 | U.S.S.R. | 128/754 |
| 1604360 | 11/1990 | U.S.S.R. | 128/754 |
| 8910091 | 11/1989 | WIPO | 128/754 |

*Primary Examiner*—Max Hindenburg
*Attorney, Agent, or Firm*—Hale and Dorr LLP

[57] ABSTRACT

A controlled surgical core biopsy system that is operated with one hand. The system includes a gun unit, a needle adapter system, and the needle assembly. The needle adapter system links the needle assembly to the gun unit. The gun unit may have a single trigger or double triggers. The single trigger embodiment requires manual insertion of the needle assembly into the tissue of interest. Once the needle assembly is manually inserted, the single trigger controls the cocking and firing of the cutting cannula over the inner stylet to trap tissue specimens in a specimen notch. As the cutting cannula is fired, the stylet and cutting cannula may be displaced vertically to facilitate the tissue specimens being trapped in the specimen notch. The double trigger embodiment, like the single trigger embodiment, requires only one hand to operate. This embodiment includes a gun unit, a needle adapter system, and a needle assembly. The double trigger embodiment requires that the needle assembly be manually inserted into the patent adjacent the tissue of interest. The upper trigger is used to advance the inner stylet and of the needle assembly a desired depth into the tissue of interest. The second trigger is used to cock and fire the outer cutting cannula to trap tissue specimens in the specimen notch of the stylet. When the outer cutting cannula is fired, the needle adapter system and the stylet may move vertically upward. This vertical movement assists in placing the tissue specimens in the specimen notch.

10 Claims, 23 Drawing Sheets

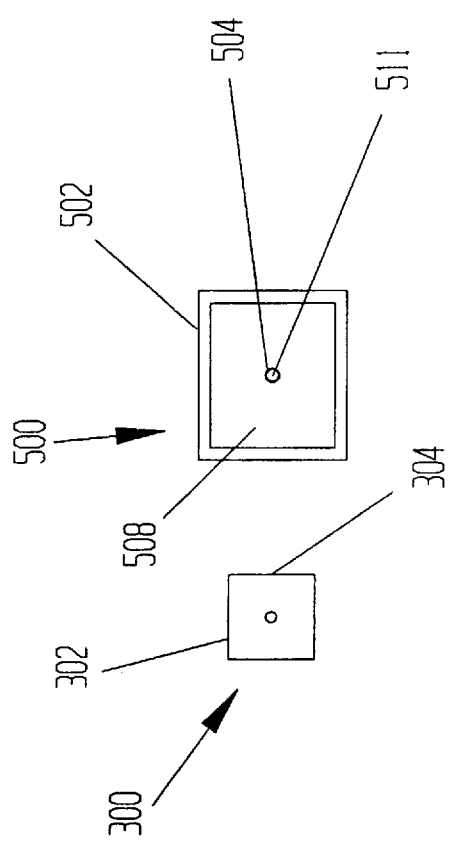

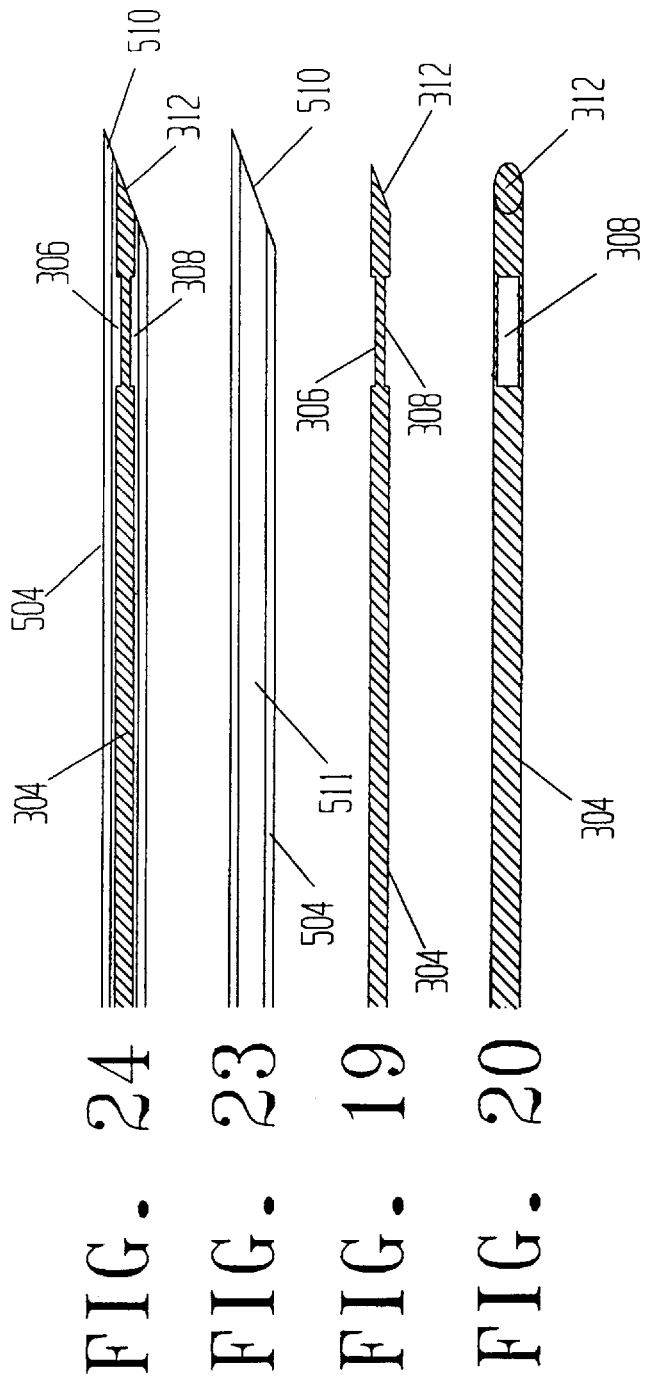

CONTROLLED SURGICAL CORE BIOPSY SYSTEM

This is a divisional of application Ser. No. 08/233,470 filed on Apr. 26, 1994, now U.S. Pat. No. 5,570,699.

FIELD OF THE INVENTION

The present invention relates to apparatuses for obtaining samples of body tissue. More specifically, the present invention relate to apparatuses used for performing core biopsies.

BACKGROUND OF THE INVENTION

In the field of medicine, before effective treatment can be prescribed, physicians normally run or have run series of tests to determine the nature of the illness, infection, or disease. Such tests, in many cases, are run on diseased tissue. This, in fact, requires the physician to obtain a specimen of the infected or diseased tissue in the most efficient manner with the least discomfort to the patient. Various biopsy methods are used to obtain these needed tissue samples.

Biopsies are performed using an open or a closed technique. Open biopsy removes the entire mass (excision biopsy) or a part of the mass (incision biopsy). Closed biopsy is usually done with a needlelike instrument and may be either an aspiration or a core biopsy. In needle aspiration biopsy, individual cells or clusters of cells are obtained for cytologic examination and may be prepared such as in a Papanicolaou smear. In core biopsy, a core or filament of tissue is obtained for histologic examination which may be done via a frozen section or paraffin section. The type of biopsy that is used depends on the circumstances; however, core biopsy is extremely useful in a number of conditions and is the most widely used type of biopsy.

A well known instrument used for core biopsies is manufactured by Travenol Laboratories of Deerfield, Ill. and is sold under the trademark "TRU-CUT". This instrument has a two piece assembly: an outer cutting cannula mounted to a hub and an inner stylet (with a specimen notch ground into it) mounted to a second hub. The two hubs are slideably interlocked.

The instrument is assembled and placed into the area of the body of interest with the outer cutting cannula just to the rear of a lancet point or beveled distal end of the stylet. The instrument is inserted up to or in front of the area to be biopsied. The stylet is then manually advanced distally in the cannula with the cannula held stationary. When the stylet is advanced into the area to be biopsied, the specimen notch is exposed and the tissue surrounding the stylet contacts the specimen notch. The outer cannula is then manually advanced distally over the stylet. This will shear off tissue which will be trapped in the specimen notch. The instrument is withdrawn with the cannula and stylet in this last position. Once the instrument is removed, the tissue specimen can be removed by advancing the stylet from within the cannula and the specimen can be tested.

The technique just described is a manual technique that requires a great deal of manual dexterity and motor coordination. More-over, it requires two hands to properly operate the instrument to obtain tissue specimens. The need to use two hands to perform this technique is a disadvantage. Further, this instrument is not reusable.

The procedure just described is somewhat complicated and there is a danger of inadvertently moving the wrong member at the wrong time. This is manifest in the two members—the stylet and cutting cannula—being at times movable together and at other times movable relative to each other to obtain tissue specimens. The person performing the biopsy inadvertently may fail to use the proper sequence of movements to effect the procedure. This can result in damage to the patient or a failure to obtain the specimen, which will require a second insertion.

The present invention overcomes the problems just described and provides a system which will permit a physician or other professional to obtain a core tissue specimen requiring the use of only one hand (allowing the other to be free for other work) and permit controlled insertion of the needle assembly to reduce the risk to the patient.

SUMMARY OF THE INVENTION

The present invention is a controlled surgical core biopsy system that is operated with one hand. The system includes a gun unit, a needle adapter system, and a needle assembly. The needle adapter system is disposed in the gun unit. The needle assembly connects to the needle adapter system and consists of an outer cutting cannula and an inner stylet. The inner stylet has at least one specimen notch for receiving tissue specimens.

The gun unit may have a single trigger or double triggers. Either embodiment of the gun unit has a size that is intended to fit in the physician's palm. The gun unit may be produced in various sizes to accommodate both large and small size hands.

The single trigger embodiment of the system of the present invention requires manual insertion of the needle assembly into the tissue of interest. The single trigger controls the cocking and firing of the cutting cannula over the inner stylet to trap a tissue specimen in the specimen notch. As the cutting cannula is fired, the stylet and cutting cannula are displaced vertically to facilitate the tissue specimen being trapped in the specimen notch.

The needle adapter system connects the needle assembly to the gun unit. The needle adapter system includes a carrier, an elongated rod, a cocking spring, and a spring cap. The elongated rod and spring cap are responsible for transmitting the movement of the gun unit to the stylet of the needle assembly. The spring cap is connected to the gun unit and the elongated rod extends through the carrier and connects to the stylet.

The spring cap, cocking spring, and carrier transmit movement of the gun unit to the cutting cannula of the needle assembly. These elements also are used to effect cocking and firing of the cutting cannula.

The double trigger embodiment of the present invention, like the single trigger embodiment, requires only one hand to operate. This embodiment includes a gun unit, a needle adapter system, and a needle assembly. The upper trigger is used to advance the inner stylet of the needle assembly into the tissue of interest once the needle assembly is manually placed adjacent the tissue of interest. The second trigger is used to cock and fire the outer cutting cannula to trap tissue specimens in the specimen notch.

In the double trigger embodiment, the needle adapter system is movable with respect to the gun unit for advancing the stylet into the tissue of interest by engaging the upper trigger and movable for cocking and firing the outer cutting cannula by engaging the lower trigger. This adds to the precision in obtaining tissue specimens.

When the outer cutting cannula is fired, it and the stylet are moved vertically upward. This vertical movement helps ensure that there is a tissue specimen in the specimen notch when the cannula moves to cut the tissue. Moreover, because the physician can control the depth the stylet is inserted in the tissue of interest, he or she also can control the amount of the specimen notch is exposed from under the distal end of the outer cutting cannula. This will permit controlling the size of the specimen obtained.

An object of the present invention is to provide a controlled surgical core biopsy system that may be operated with one hand.

Another object of the present invention is to provide a controlled surgical core biopsy system that has a gun unit and needle adapter system that are reusable without sterilization.

A further object of the present invention is to provide as controlled surgical core biopsy system in which the needle assembly is movable in the vertical direction to insure that there is a tissue specimen in the specimen notch of the stylet when the outer cutting cannula is fired.

A still further object of the present invention is to provide a controlled surgical core biopsy system that permits controlling the size of tissue specimen obtained.

A yet further object of the present invention is to provide a controlled surgical core biopsy system in which the needle assembly is loaded on the needle adapter system at the front of the gun unit.

These and other objects will be explained in greater detail in the remainder of the specification referring to the attached drawings.

BRIEF DESCRIPTION OF THE DRAWINGS

FIG. 10B is an end view of end of the elongated rod shown in FIG. 10A.

FIG. 18 is a front end view of the stylet for the single and double trigger embodiment of the controlled surgical core biopsy system of the present invention.

FIG. 19 is a side view of the distal end of the stylet of the needle assembly.

FIG. 20 is a bottom view of the distal end of the stylet of the needle assembly.

FIG. 22 is a rear end view of the cutting cannula assembly of the needle assembly for the single or double trigger embodiment of the controlled surgical core biopsy system of the present invention.

FIG. 23 is a cross-sectional view of the distal end of the cutting cannula assembly of the needle assembly for the single or double trigger embodiment of the controlled surgical core biopsy system of the present invention.

FIG. 24 is a cross-sectional view of the distal ends of the stylet and cutting cannula as aligned for insertion into the patient and after the cutting cannula has been fired.

DETAILED DESCRIPTION OF THE DRAWINGS

Figure 1:
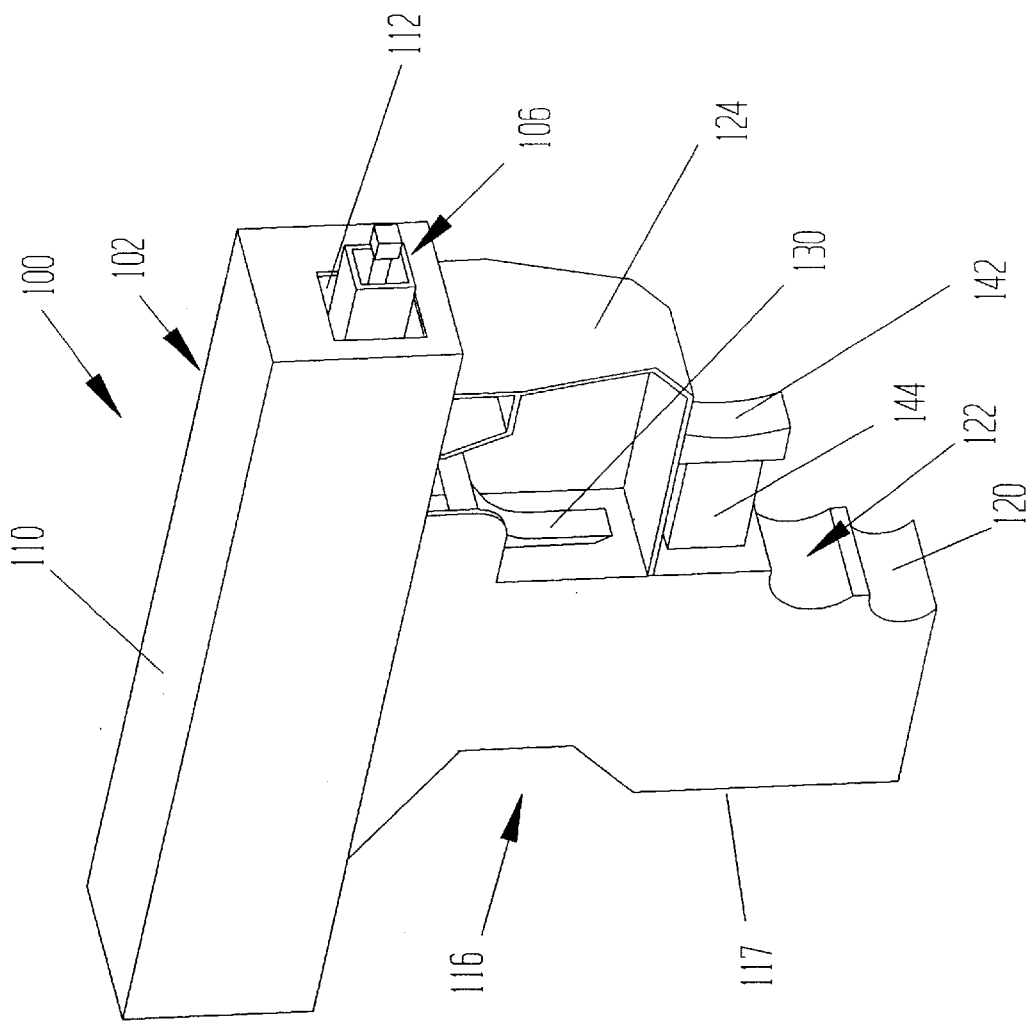
FIG. 1 is a top perspective view of the double trigger embodiment of controlled surgical core biopsy system of the present invention without the needle assembly attached.
Figure 2:
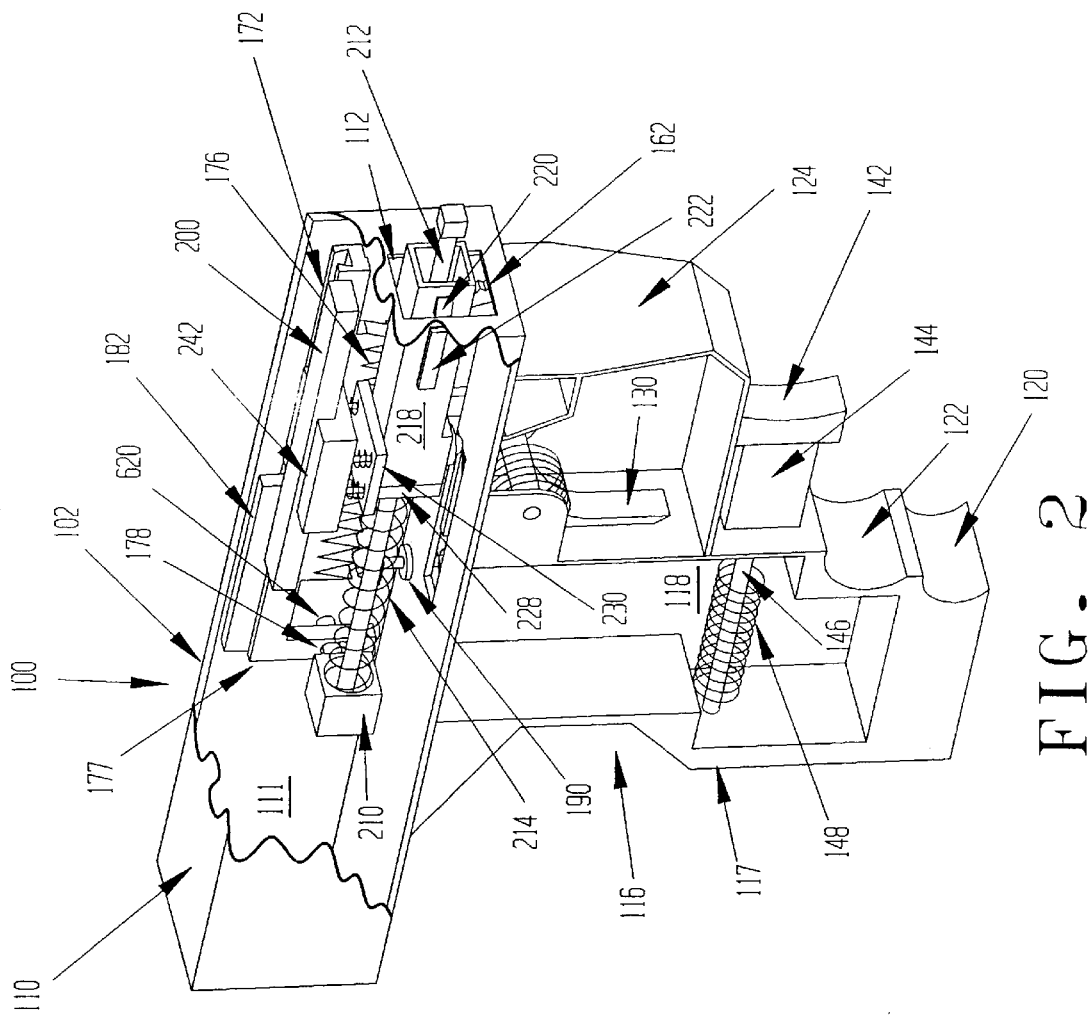
FIG. 2 is a top perspective view of FIG. 1 with a portion of the housing removed.

The present invention is a controlled surgical core ("CSC") biopsy system that may be used to obtain tissue specimens for testing and evaluation. FIGS. 1 and 2, generally at 100, show top perspective views of the double trigger embodiment of the CSC biopsy system of the present invention. The double trigger embodiment of the CSC biopsy system includes gun unit 102, needle assembly 104 (FIG. 16), and needle adapter system 106. Needle adapter system 106 is used to connect needle assembly 104 to gun unit 102. The reusable part of the CSC biopsy system of the present invention is gun unit 102 and needle adapter system 106; the disposable part is needle assembly 104. Each of these elements of the double trigger embodiment of the CSC biopsy system of the present invention will be described in detail referring to FIGS. 1–24.

FIG. 1 shows a top perspective view of the double trigger embodiment of the CSC biopsy system. This Figure shows the outer housing structure of gun unit 102 with the end of needle adapter system 106 extending from the front. The end of needle adapter system 106 extends from the front end of gun unit 102 to facilitate front loading needle assembly 104.

FIG. 2 shows the same top perspective view of the CSC biopsy system of the present invention with part of the outer housing structure of gun unit 102 removed so that the interior elements can be viewed.

Figure 3:
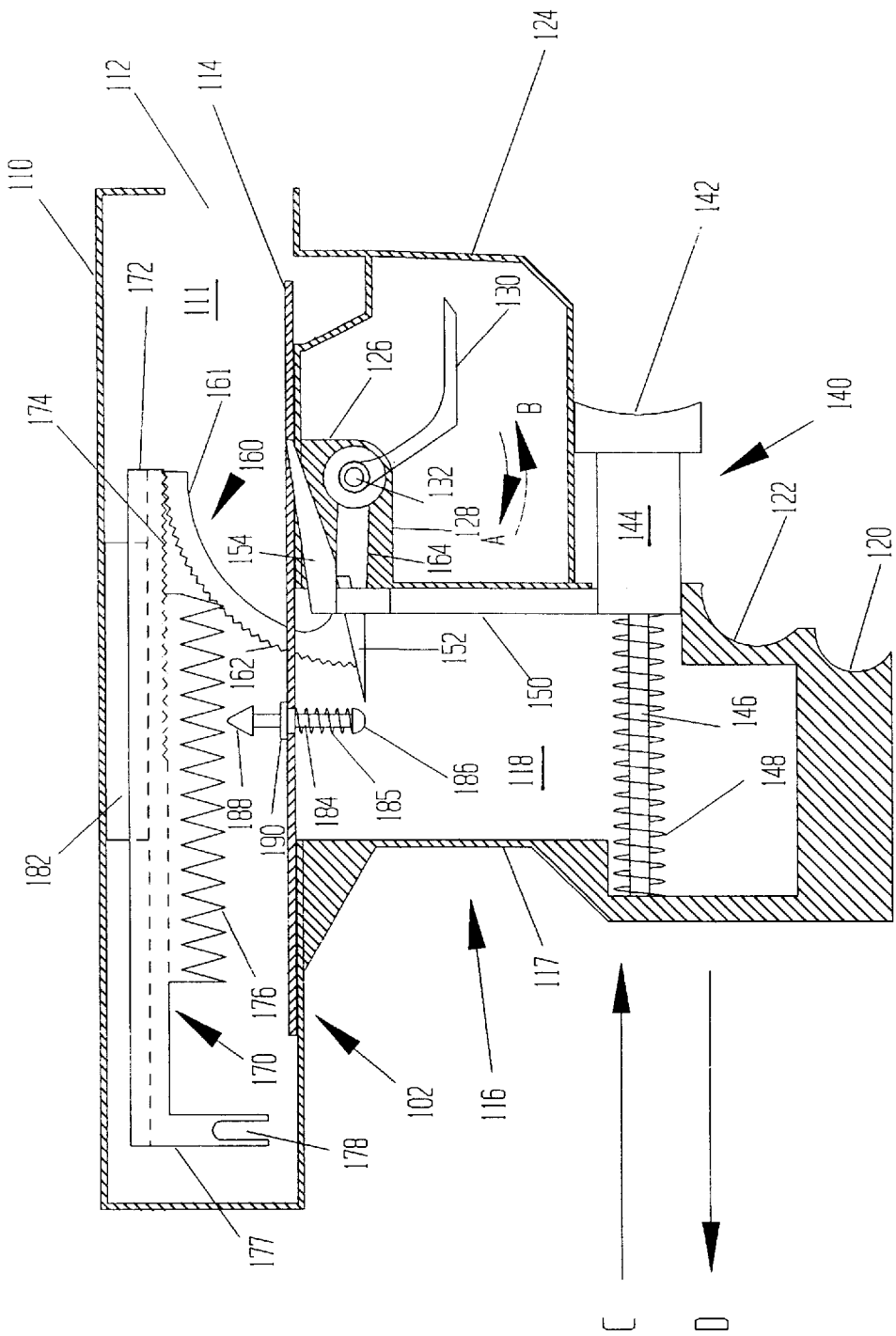
FIG. 3 is a longitudinal cross-sectional view of the gun unit of the double trigger embodiment of the controlled surgical core biopsy system of FIG. 1 with the upper and lower triggers unengaged.
Figure 4:
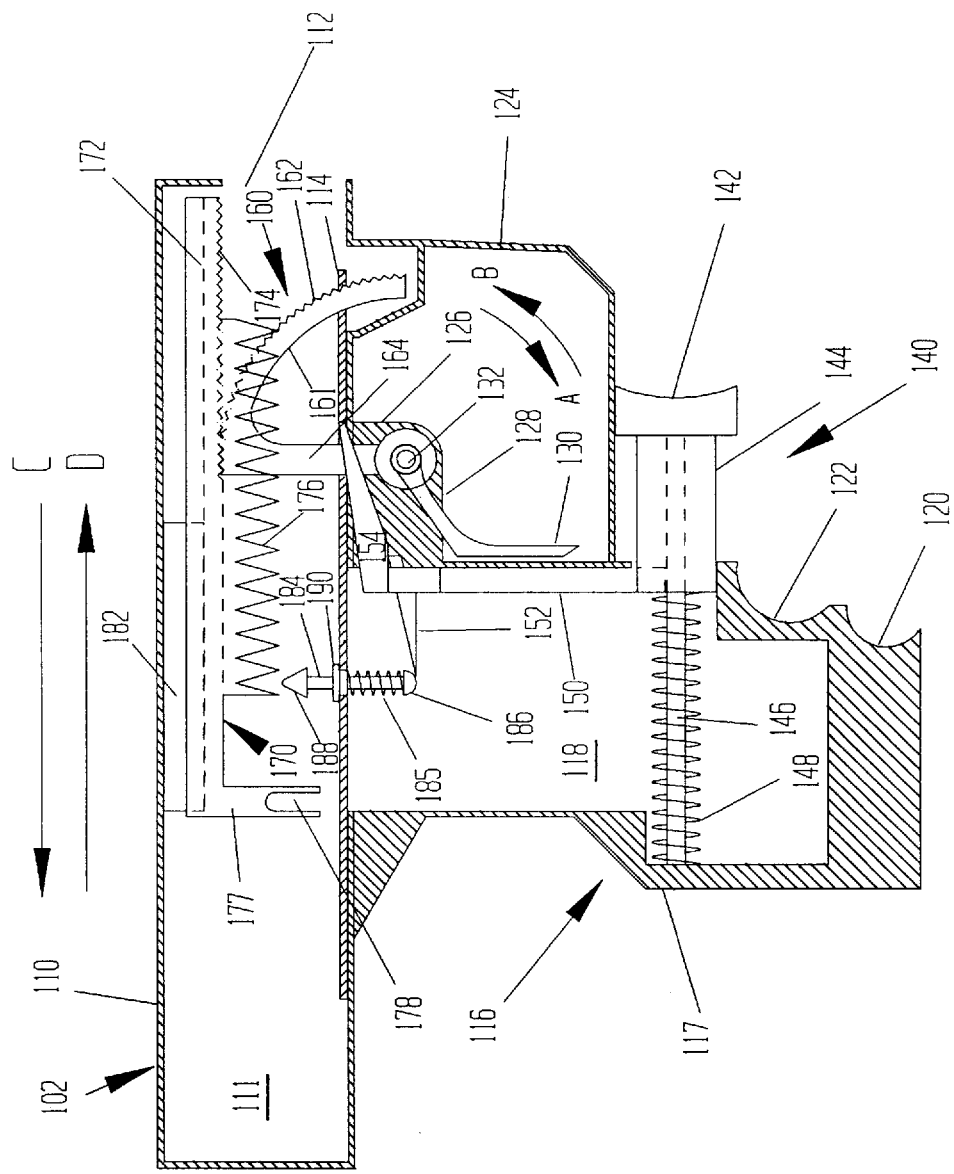
FIG. 4 is a longitudinal cross-sectional view of the gun unit of the double trigger embodiment of the controlled surgical core biopsy system of FIG. 1 with the upper trigger engaged and the lower trigger unengaged.

FIGS. 3 and 4 show two cross-sectional views of the gun unit of the double trigger embodiment of the CSC biopsy. The differences in these two Figures is that in FIG. 3 the upper trigger is unengaged and in FIG. 4, the upper trigger is engaged. As will be shown, movement of the upper trigger will advance stylet 300 of needle assembly 104 into the tissue of interest.

Referring to FIGS. 1–4, and 7, gun unit 102 will be described. This description will discuss gun unit 102 and its mechanism for translating upper trigger movement into a movement for advancing stylet 300 of needle assembly 104 into the tissue of interest.

Gun unit 102 includes upper portion 110, handle body 116, and trigger guard assembly 124. Upper portion 110 includes open area 111, and has rectangular opening 112 in a first end and a closed second end. Horizontally disposed flat members 114, which have a channel between them (FIG. 7), form part of the bottom of the upper portion of gun unit 102. Handle body 116 has portion 117, which is meant to fit into the physician's or professional's palm, and finger grips 120 and 122 that are for the little and ring fingers, respectively. The index finger is used to control upper trigger 130 and the middle finger to control lower trigger 142.

Figure 7:
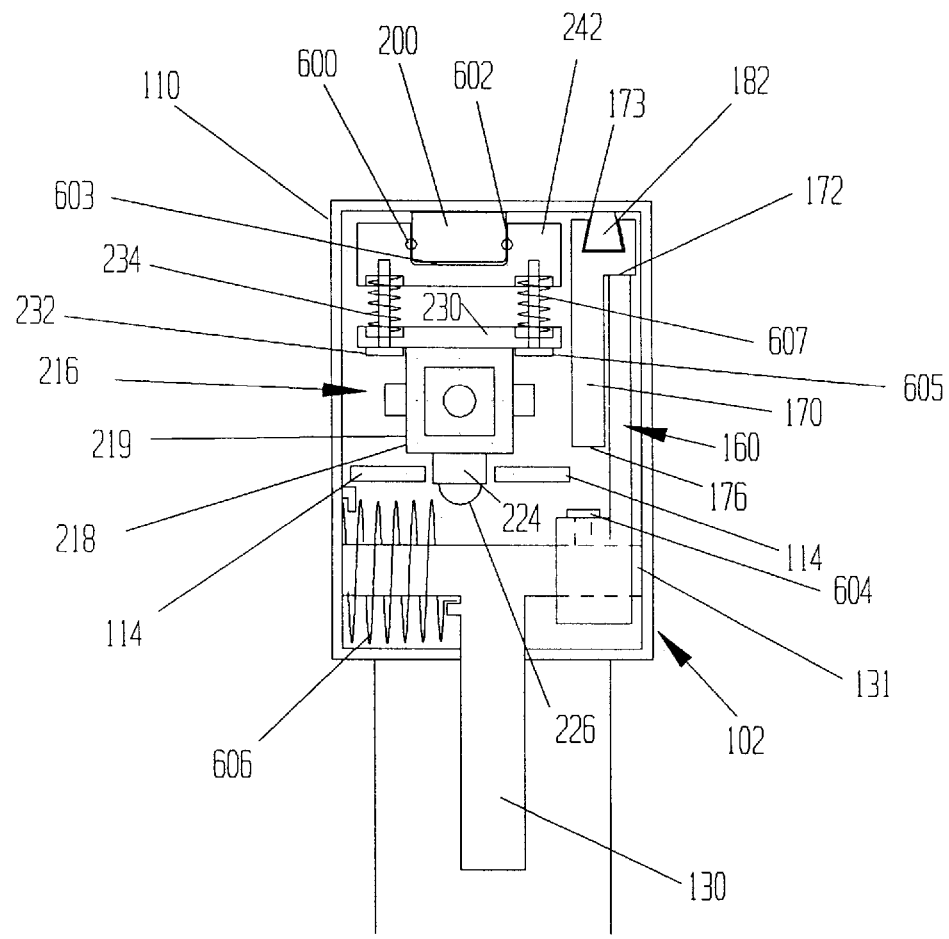
FIG. 7 is a partial lateral cross-sectional view of the double trigger embodiment of the controlled surgical core biopsy system of the present invention.
Figure 8:
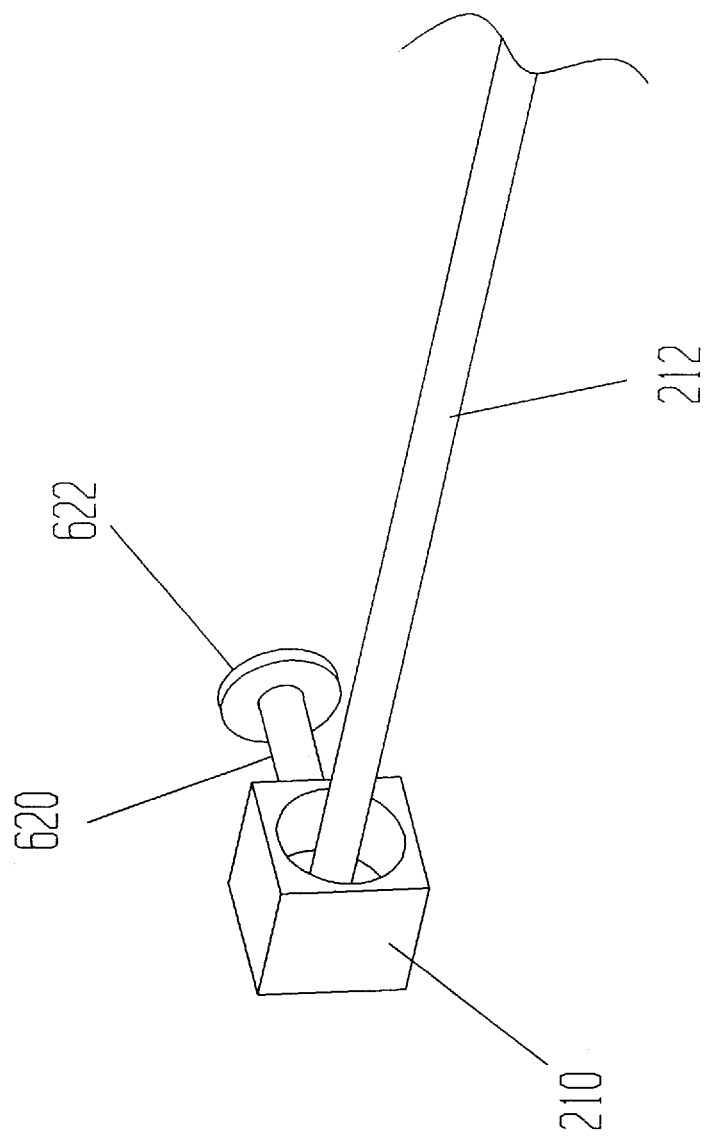
FIG. 8 is a cross-sectional view of the drive cap and elongated rod of the needle adapter system that is used to connect the stylet of the needle assembly to the gun unit.
Figure 9:
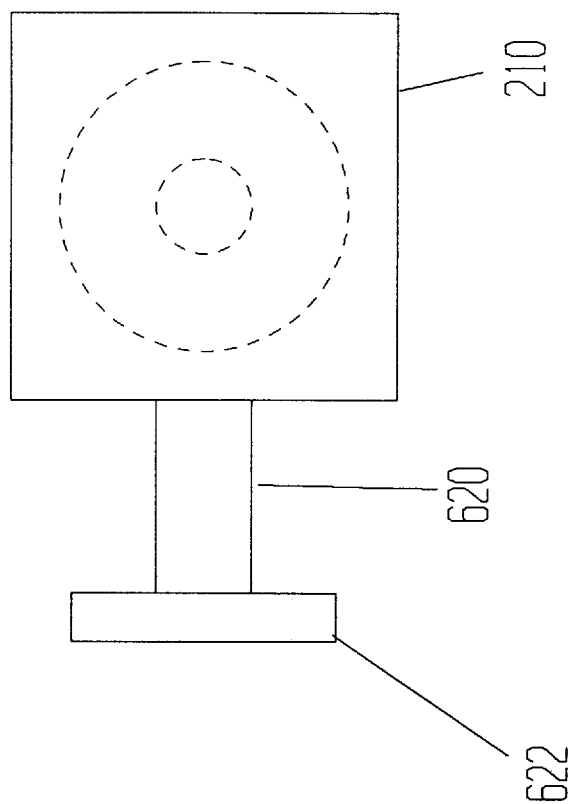
FIG. 9 is an end view of the drive cap and drive rod of the needle adapter system that is used to connect the stylet of the needle assembly to the gun unit.
Figure 10:
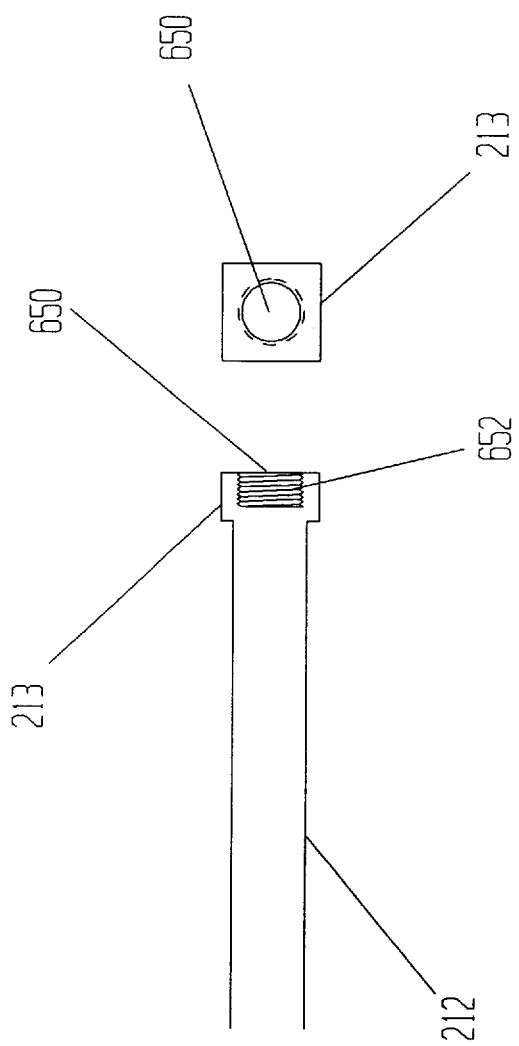
FIG. 10 A is a cross-sectional view of the end of the elongated rod of the needle adapter system that connects to the stylet of the needle assembly of the gun unit.

Rack guide 182 (shown partially in phantom) is fixed to the top, inside surface of upper portion 110. Rack guide 182 has a trapezoidal cross-sectional shape and is disposed closer to one of the side walls as shown in FIG. 7.

Elongated rack element 170 has top member 172, toothed lock member 176, and driving end member 177. Top member 172 has an elongated channel 173 cut in its top surface. This channel has a trapezoidal cross-sectional shape which is slightly larger than that of rack guide 182 so that elongated rack element 170 will mate with, and ride smoothly in directions "C" and "D" on, rack guide 182.

Top member 172 has rack members 174 disposed along its bottom surface. These rack members run a desired length along the bottom surface of top member 172.

Toothed lock member 176 is disposed downwardly from top member 172 closer to one side of top member 172 so not to interfere with the engagement of rack members 174 by a mating gear member. Toothed lock member 176 preferably is rectangular in shape and has a sawtooth bottom edge. Toothed lock member 176 extends only a portion of the length of top member 172. The toothed lock member works with a locking pin to prevent forward or backward movement of needle assembly 104 when the cutting cannula assembly is being fired to trap a tissue specimens in the specimen notch.

Elongated rack element 170 has driving end member 177 that includes downwardly disposed opening 178. This opening receives a portion of needle adapter system 106 so that movement of upper trigger 130 is translated to movement of needle assembly.

Upper trigger 130 is connected to trigger shaft 131 (FIG. 7). Trigger guard assembly 124 has trigger shaft receiver 132 that is connected to end member 128. Trigger guard assembly 124 also has end member 126 that has a shape that will permit trigger shaft 131 to rotate in directions "A" and "B". Return spring 606 (FIG. 7) is connected to trigger 130 to return the trigger to its initial position once it is no longer engaged by the index finger, for example, of the physician.

Pinion gear assembly 160 connects to trigger shaft 131. Pinion gear assembly 160 includes arcshaped pinion gear 161 with teeth 162 and connecting member 164 that connects pinion gear 161 to trigger shaft 131. The pinion gear assembly may be connected to trigger shaft 131 by pin 604 (FIG. 7).

In operation, if upper trigger 130 is engaged with the index finger and rotated in direction "A," pinion gear 161 and rack members 172 cause elongated rack element 170 to move in direction "C." The amount that elongated rack element 170 moves in direction "C" is determined by the amount upper trigger 130 is rotated. This remains true as long as lower trigger 142 is not engaged.

When upper trigger 130 is released, return spring 606 will rotate upper trigger 130 in direction "B," which in turn, through pinion gear 161 and rack members 174, will move elongated rack element 170 in direction "D" back to its initial position. This will be explained in detail subsequently. The movement of elongated rack element 170 in directions "C" and "D" permits the physician to insert stylet 300 of needle assembly 104 into the tissue of interest to a desired depth with great precision and remove it with the same precision.

Pin 184 with downwardly disposed head 186 extends through flat member 114. The pinhead is biased downwardly by spring 185. Collar 190 at the top surface of flat member 114 prevents pin 184 from passing through flat plate 114 when biased by spring 185 but will allow the pin to moving upwardly against spring 185. When pin 184 is forced upwardly against spring 185, end 188 of pin 184 will engage the saw-tooth bottom edge of toothed lock member 176. When end 188 engages toothed lock member 176, elongated rack element 170 is locked from movement in direction "C" or "D." When this happens, the stylet of the needle assembly 104 will be held stationary while the cutting cannula assembly of the needle assembly 104 may be cocked and fired to trap a tissue specimen in the specimen notch.

Referring to FIGS. 1, 2, 5–7, and 13, the lower trigger assembly of gun unit 102 and its operation will be described.

Figure 5:
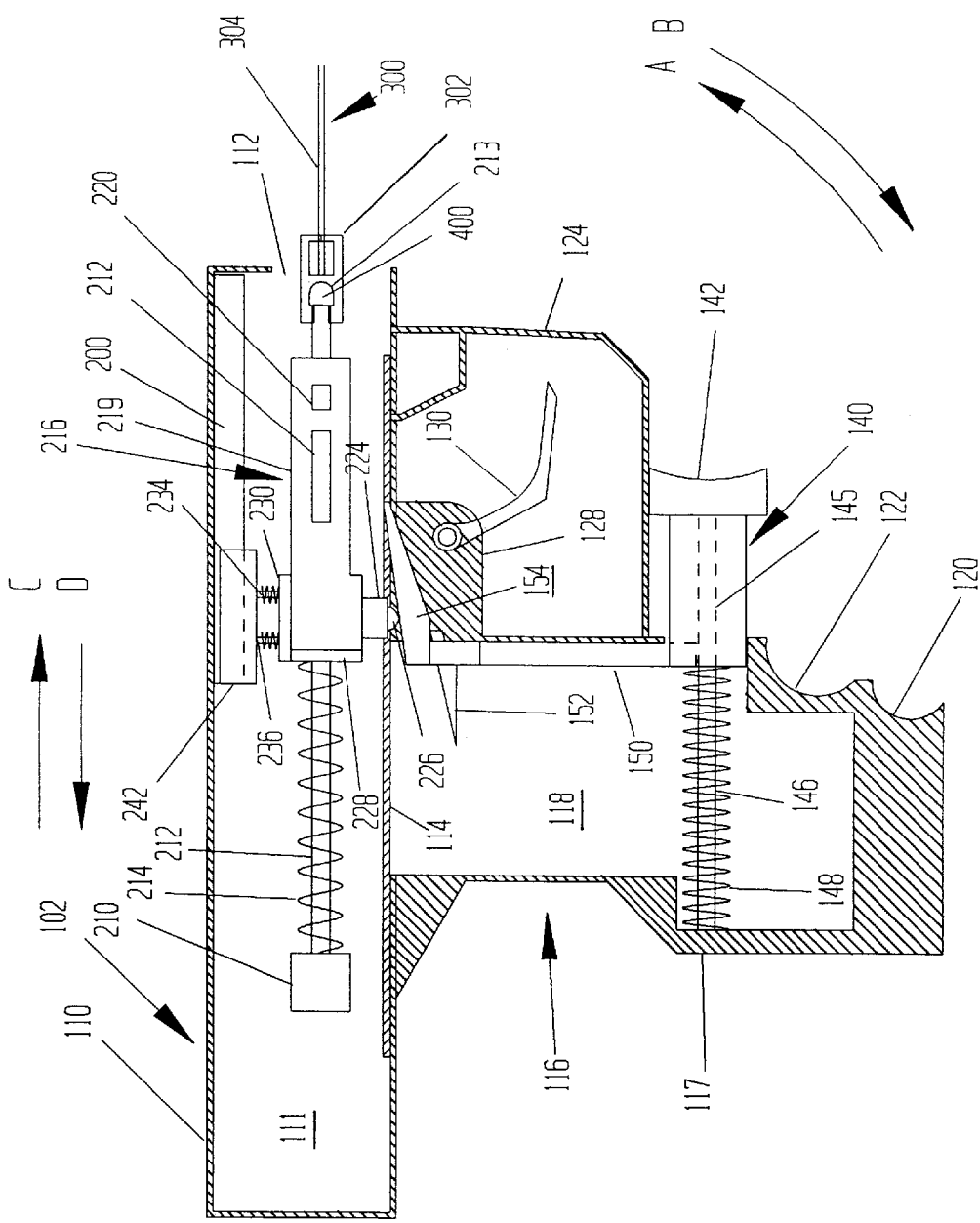
FIG. 5 is a longitudinal cross-sectional view of the gun unit of the double trigger embodiment of the controlled surgical core biopsy system of FIG. 1 with the upper and lower triggers unengaged, and it shows the needle adapter system and part of the needle assembly.
Figure 6:
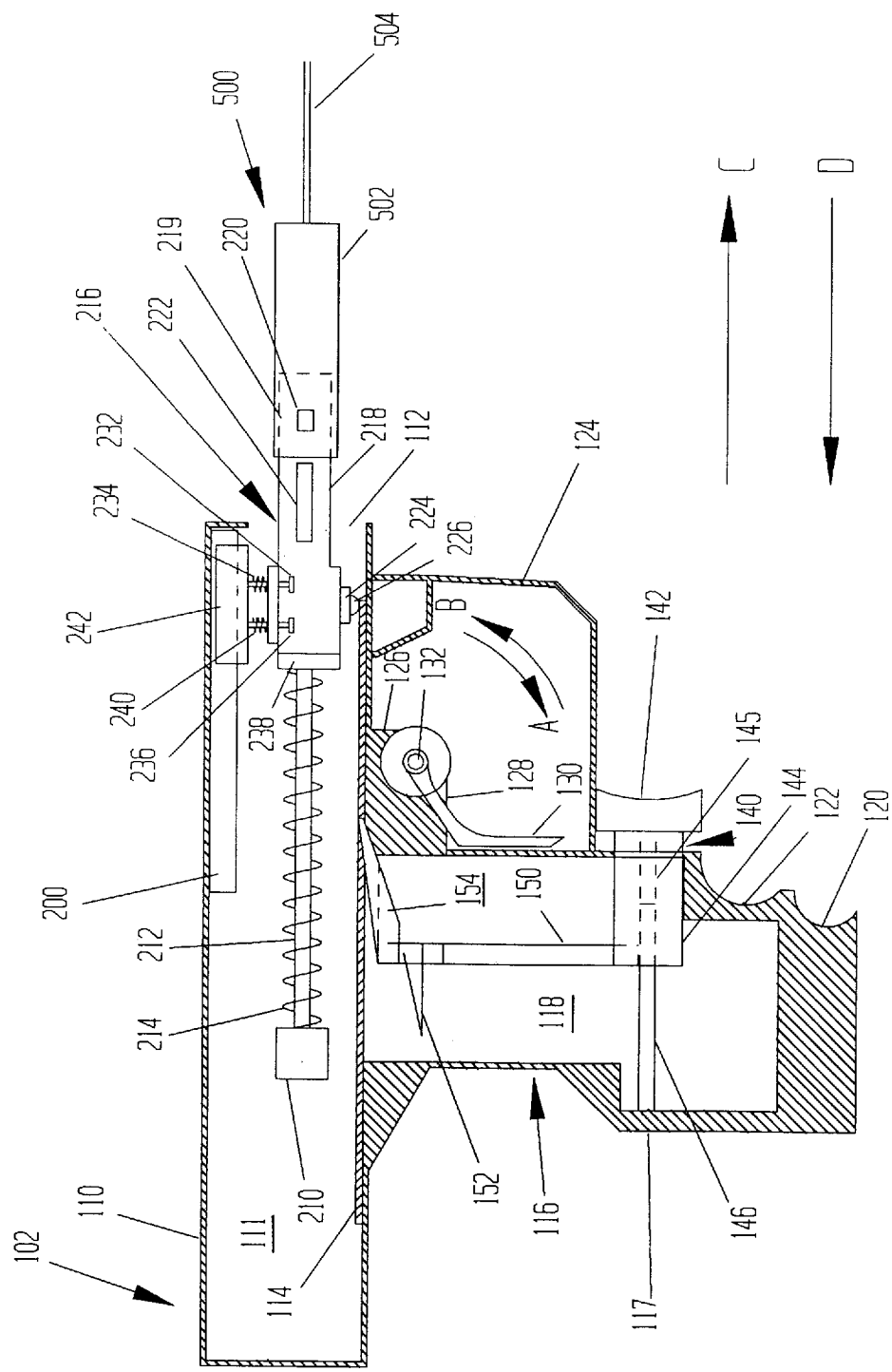
FIG. 6 shows a longitudinal cross-sectional view of the gun unit of the double trigger embodiment of the controlled surgical core biopsy system of FIG. 1 with the upper and lower triggers, and it shows the needle adapter system and part of the needle assembly.
Figure 13:
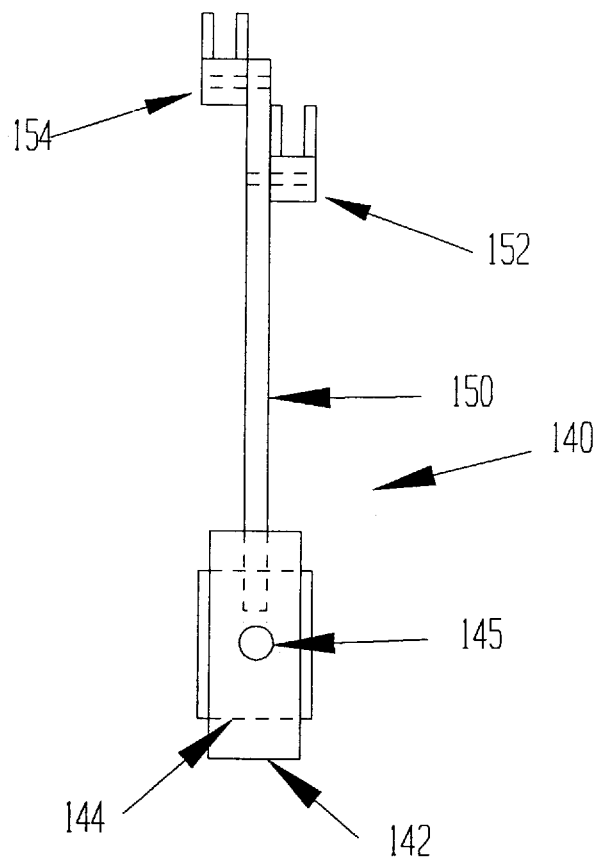
FIG. 13 is a front end view of the lower trigger assembly of the gun unit of the double trigger embodiment of controlled surgical biopsy system.

Referring to FIGS. 5 and 13, gun unit 102 has lower trigger assembly 140 that rides on guide rod 146 that extends forward across opening 118 from the rear inside wall of handle body 116. Lower trigger assembly 140 includes trigger body 144 that has trigger head 142 fixed at a first end and vertical member 150 disposed upwardly from the second end. Trigger body 144 has central bore 145 that slideably receives guide rod 146. This permits lower trigger assembly 140 the move in directions "C" and "D" guided by guide rod 146. Vertical member 150 has locking pin driver 152 that extends rearward and cocking member 154 that extends forward.

In operation, when lower trigger assembly 140 is moved in direction "D," the upwardly sloping top surface of locking pin driver 152 contacts head 186 of pin 184 driving end 188 upwardly to engage the saw-tooth bottom edge of toothed lock member 176 for the purpose described previously. Cocking member 154 has an upwardly sloping top surface which is longer than the upwardly sloping top surface of locking pin driver 152. This is so locking pin 184 will lock movement of the stylet before cocking takes places.

Guide rod 146 has return spring 148 disposed around it. A first end of this spring contacts second end of lower trigger body 144 and the second end of spring 148 contacts the inside, rear wall of handle body 116. When the lower trigger is engaged and moved in direction "C," return spring 148 is compressed; and when the lower trigger is no longer engaged, spring 148 will more the trigger assembly in direction "D" back to its original position.

Referring to FIGS. 1, 2, and 5–15 , needle adapter system 106 will be described. Needle adapter system 106 includes drive cap 210 elongated rod 212, cocking spring 214, and cutting cannula carriage assembly 216. These elements are used to connect needle assembly 104 to gun unit 102.

Referring to FIGS. 2, 5, 6, and 8–12, drive cap 210 is a hollow, cylindrical-shaped member with one open end. Elongated rod 212 is disposed in the open end of the drive cap and fixed to its rear wall. Drive cap 210 has drive rod 620 extending perpendicularly outward from a side wall. Capture cap 622 is disposed at the distal end of drive rod 620.

Drive rod 620 is disposed in opening 178 of driving end member 177 of elongated rack element 170. Capture cap 622 at the end of drive rod keeps drive rod 620 from passing out of opening 178.

The distal end of elongated rod 212 connects to stylet 300 of needle assembly 104. Referring to FIGS. 10A and 10B, elongated rod 212 has universal end 213 to which stylet connecting member 400 connects. Universal end 213 has opening 650 that may have flutes 652 to prevent stylet connecting member 400 from turning in universal end 213.

Figure 11:
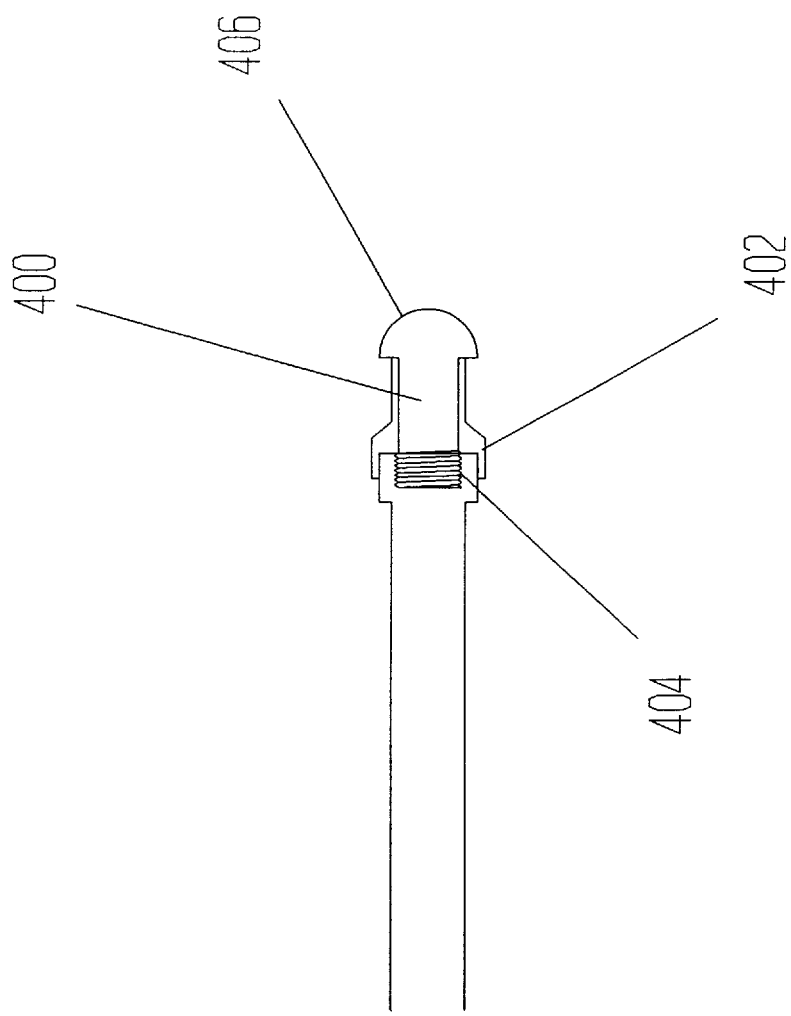
FIG. 11 is a cross-sectional view of the end of the elongated rod of the needle adapter system shown in FIG. 10A with a connecting member attached.

FIG. 11 shows irregular shaped stylet connecting member 400 which attaches to universal end 213. Stylet connecting member 400 has body 402, head 406, and fluted extension 404 for mating with universal end 213. Although a specific shape of stylet connecting member 400 is shown in FIG. 11, the shape of this member can be any shape that will permit elongated rod 212 to connect to stylet 300 of needle assembly 104 in a locking relationship.

Figure 12:
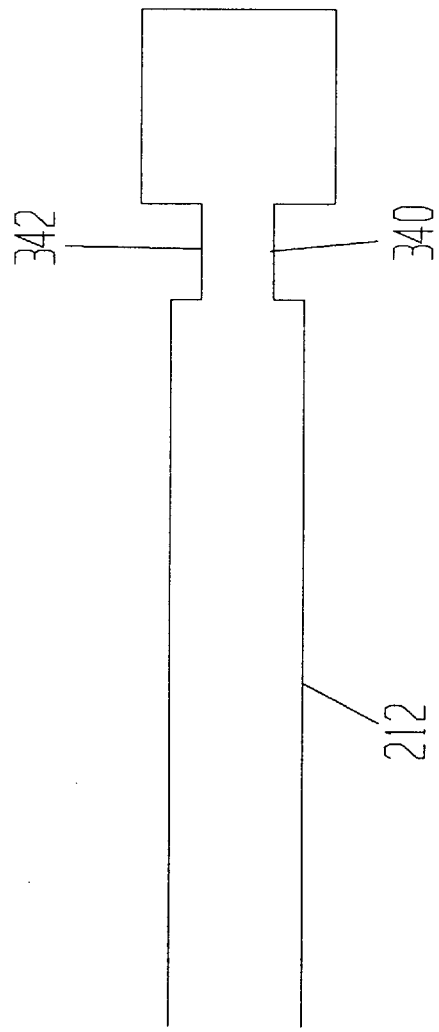
FIG. 12 is a cross-sectional view of another embodiment of the end of the elongated rod of the needle adapter system.

FIG. 12 shows another embodiment for the shape of the end of elongated rod 212. Here, the end of the elongated rod has cut outs 340 and 342 spaced back from the distal end. This embodiment is meant to mate directly with the end of stylet 300 in a locking relationship. Other shapes may be used for the end of the elongated rod as long as such shapes will permit the end of elongated rod 212 and stylet 300 to mate in a locking relationship.

Referring to FIGS. 2, 5, 6, 7, 14, and 15, cutting cannula carriage assembly 216 will be described.

Cutting cannula carriage assembly 216 includes carriage guide block 242, hollow carriage connector 218, four pins for connecting carriage guide block 242 and hollow carriage connector 218, and receiver 224 with ball bearing 226 disposed in it.

Carriage guide 200 is connected to top inside surface of upper portion 110 and is part of gun unit 102. Carriage guide block 242 has channel 603 that receives carriage guide 200. Bearing sets 600 and 602 are disposed between carriage guide block 242 and carriage channel 603 to facilitate smooth movement of the carriage guide block in directions "C" and "D."

Carriage guide block 242 has four downwardly disposed pins extending from its bottom surface. All four pins are shown in the Figures. Specifically, FIG. 14 shown pins 232 and 236, FIG. 7 shows pin 605, and FIG. 15 shows pin 703.

Figure 14:
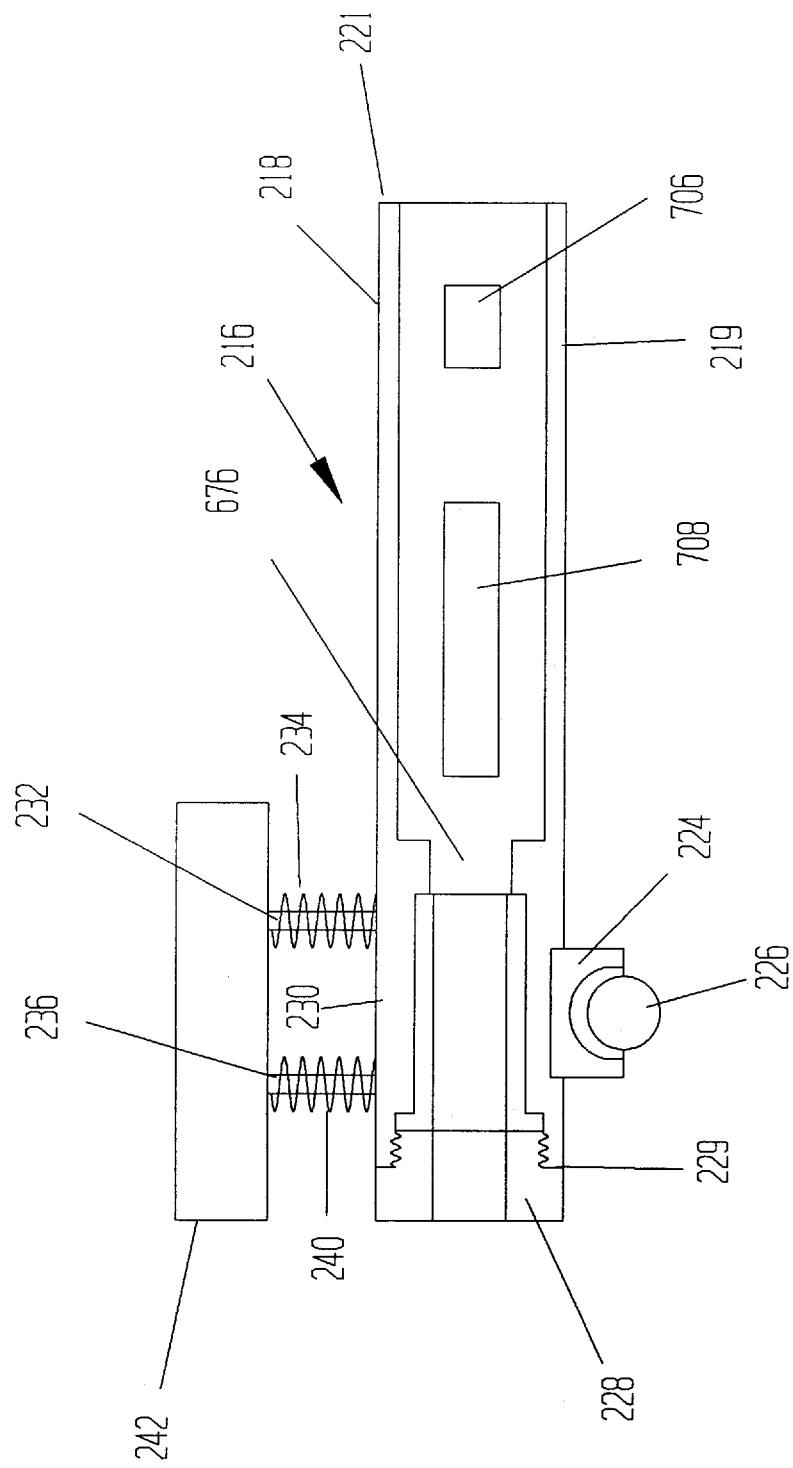
FIG. 14 is a partial cross-sectional view of the carriage assembly of the needle adapter system of the double trigger embodiment of the controlled surgical core biopsy system.
Figure 15:
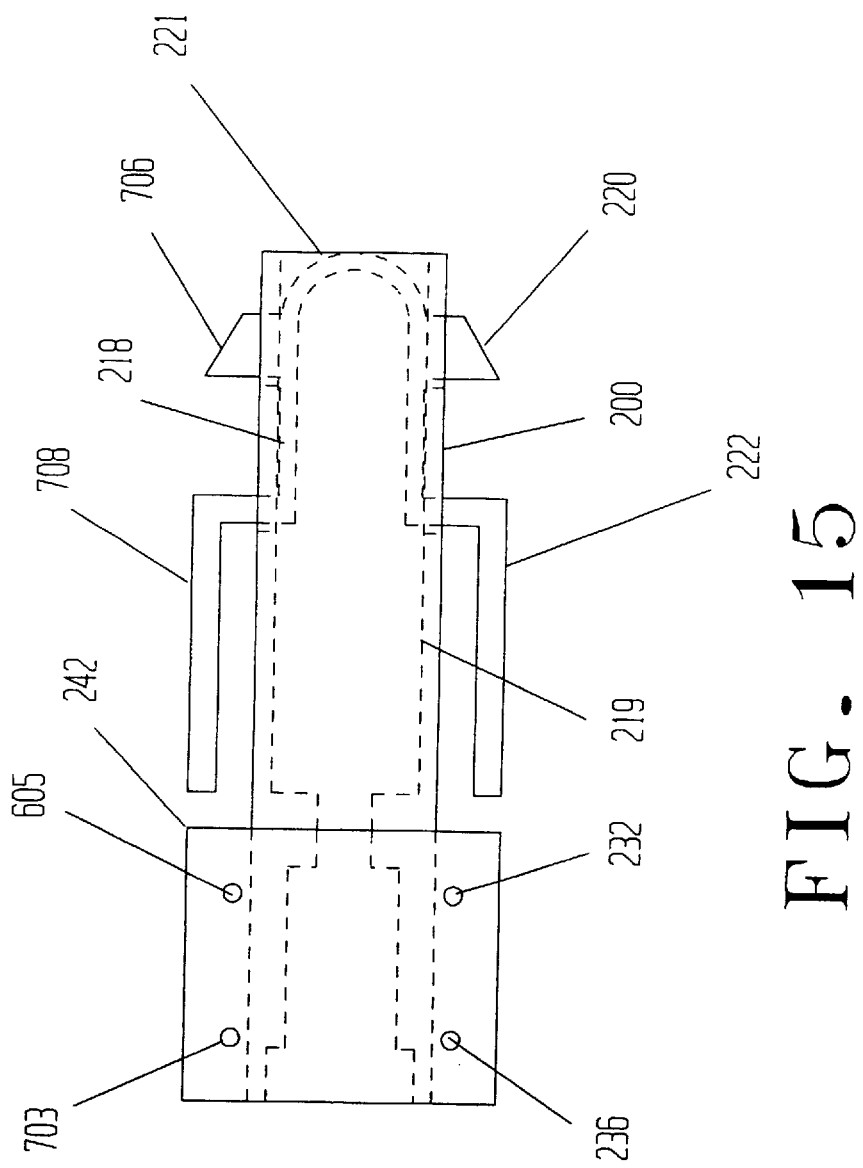
FIG. 15 is a top view of the carriage assembly of the needle adapter system of the double embodiment of the controlled surgical core biopsy system.

Hollow carriage connector 218 connects to the four pins disposed from the bottom surface of carriage guide block 242 at plate member 230 (FIGS. 7 and 14). Each of the pins has an end of sufficient size to prevent it from passing out of the hole in upper plate member 230 through which it extends.

Each of the four pins has a biasing spring around it between carriage guide block 242 and upper plate member 230. With regard to the three pins that are shown, spring 234 is associated with pin 232, spring 240 with pin 236, and spring 607 with pin 605. These springs along with the one for fourth pin 703 (not shown) bias hollow carriage connector 218 downwardly for cocking and firing cutting cannula assembly 500.

Hollow carriage connector 218 has body 219. First end 221 of body 216 is rounded (FIG. 15) to make it easier to mate with the end of the cutting cannula assembly. Spaced back from the rounded front end of body 219 and extending from the sides of the body are cannula locking members 220 and 706. The cannula locking members are used to connect cutting cannula carriage assembly 216 and the end of cutting cannula assembly 500 of needle assembly 104. Cannula locking members 220 and 706 are depressible into body 219 for connecting and disconnecting cutting cannula assembly 500.

Spaced back further from the rounded front end of body 219 and also extending from the sides of the body are stop members 224 and 708. The stop members are used to stop the rearward movement of the end of cutting cannula assembly 500 when it is connected to hollow carriage connector 218.

The bottom of body 219 has ball bearing receiver 224 extending downwardly from it. Ball bearing 226 is inserted in the open end of ball bearing receiver 224 and freely rotates in the receiver. Ball bearing 226 contacts the upwardly sloping surface of cocking member 154 of lower trigger assembly 140.

Second end 228 of end of body 219, opposite rounded first end 221, has flange 229 that serves as a stop for cocking spring 214. The use of this spring will be described in detail subsequently.

When needle adapter system 106 is connected to gun unit 102, drive rod 620 of drive cap 210 is disposed through opening 178 of driving end member 177. Elongated rod 212, which extends from drive cap 210, is disposed through body 219 of hollow carriage connector 218. Spring 214 is disposed over elongated rod 212 with a first end against flange 229 of body 219 and a second end fixed in drive cap 210.

Referring to FIGS. 16–24, needle assembly 104 will be described. First the stylet will be described, then the cutting cannula assembly will be described.

Figure 16:
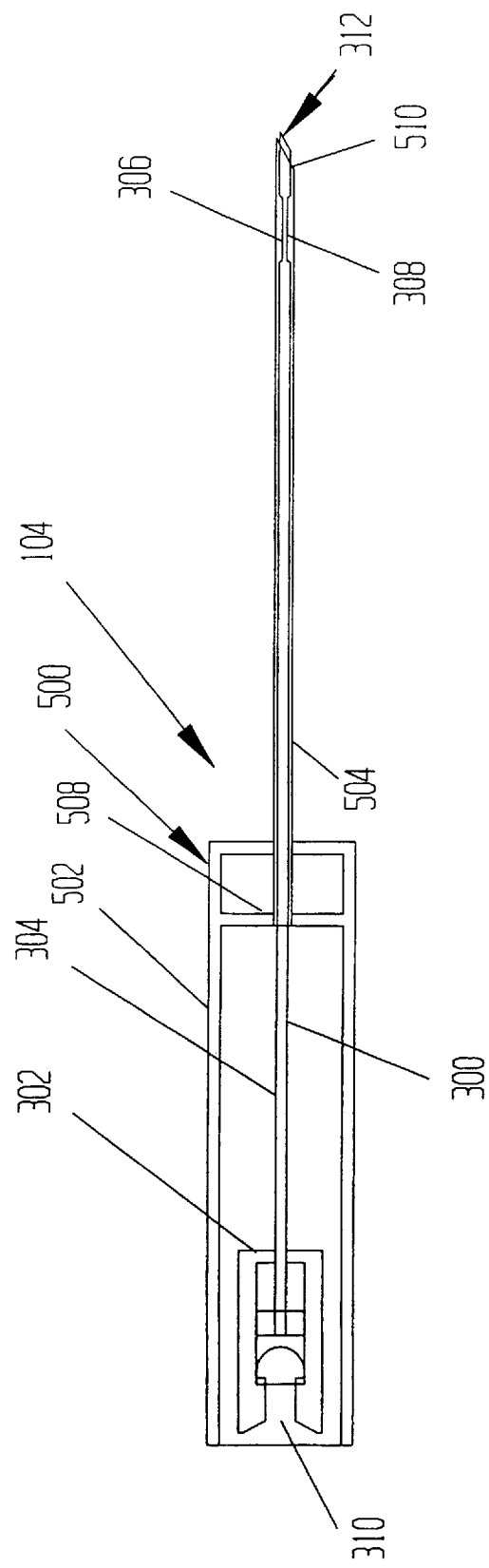
FIG. 16 is a cross-sectional view of the needle assembly for the single or double trigger embodiment of the controlled surgical core biopsy system of the present invention.
Figure 17:
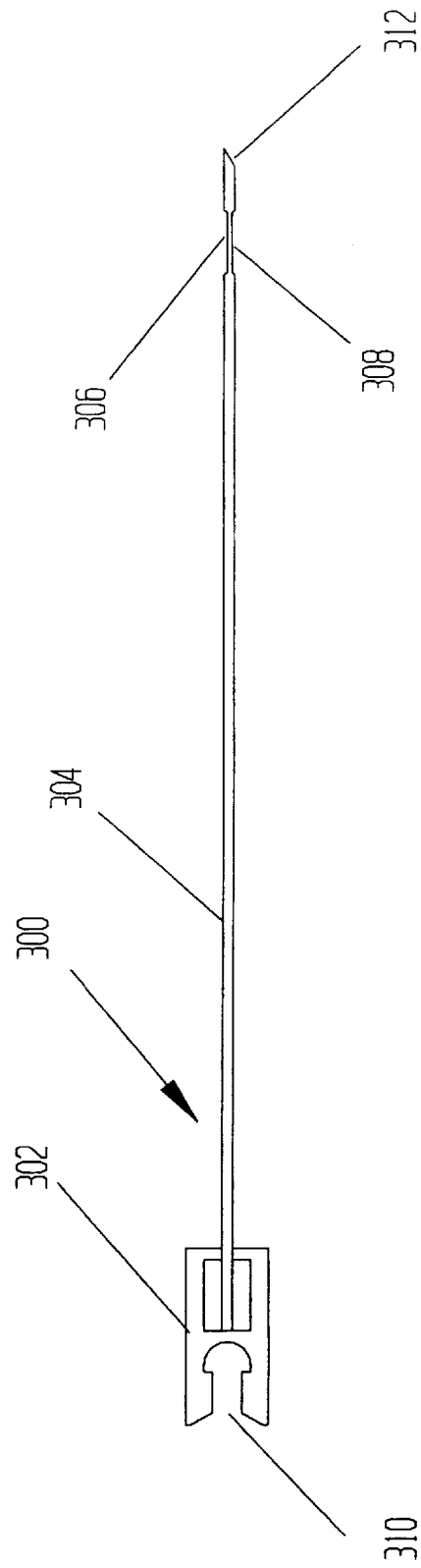
FIG. 17 is a cross-sectional view of the stylet for the single or double trigger embodiment of the controlled surgical core biopsy system of the present invention.

FIG. 16 shows a cross-sectional view of the relationship between the stylet 300 and cutting cannula assembly 500 when needle assembly 104 is assembled. A cross-sectional view of stylet 300 is shown in FIG. 17. A front end view of stylet 300 is shown in FIG. 18.

Stylet 300 has connection block 302 and needle section 304. Connection block 302 has female lock opening 310 that has an irregular shape that will mate with the irregular shape of stylet connecting member 400 at distal end of elongated rod 212. Preferably, connection block 302 has a square lateral cross-sectional shape as shown in the front end view in FIG. 18. It is understood, however, that the cross-sectional shape of connection block 302 may be other than square and still within the scope of the present invention.

Referring to FIGS. 17, 19, and 20, needle section 304 has a second end fixed in connection block 302. First end 312 of needle section 304 is distal from connection block 302 and beveled. Spaced back from first end 312 are opposing areas 306 and 308 that are cut in the needle section body. These areas are specimen notches for receiving tissue that has been cut by cutting cannula assembly 500, as will be described. These notches can vary in length depending on the maximum desired size of the tissue specimen.

Figure 21:
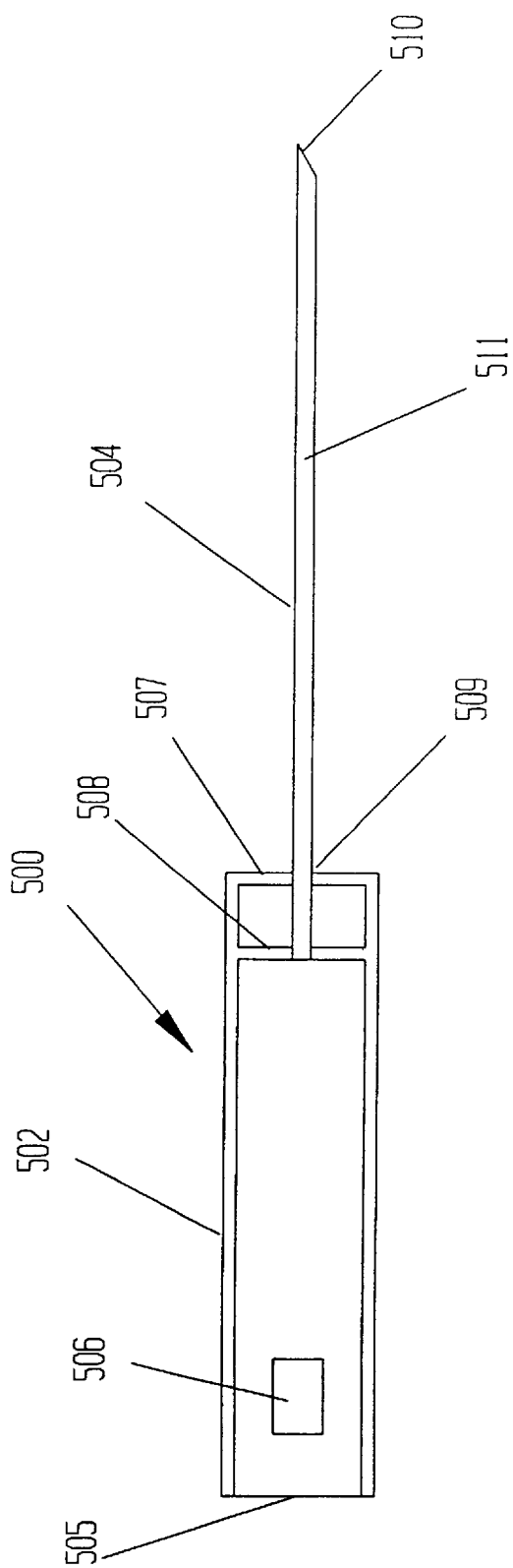
FIG. 21 is a cross-sectional view of the cutting cannula assembly of the needle assembly for the single or double trigger embodiment of the controlled surgical core biopsy system of the present invention.

Referring to FIGS. 21, 22, and 23, cutting cannula assembly 500 includes elongated connection member 502 and cutting cannula 504. Elongated connection member 502 is hollow and has a rectangular, longitudinal cross-sectional shape. The rear end view in FIG. 22 shows the exterior and opening of elongated connection member 502 are square in lateral cross-section. The lateral cross-section of shape of the square opening in elongated connection member 502 is slightly larger than the square lateral cross-sectional shape of connection block 302 of stylet 300 so that connection block 302 can slide freely in elongated connection member 502. Although these are the preferred shapes, other shapes that will permit the cooperative movement between stylet 300 and cutting cannula assembly 500 may be used and such shapes will still be in the scope of the present invention.

Spaced a short distance forward from second end 505 of elongated connection member 502 are locking openings 506. Preferably, these locking openings are through opposing side walls of elongated connection member 502 and are rectangular in shape. These locking openings receive cannula locking members 220 and 706.

First end 507 of elongated connection member 502 has opening 509 through which cutting cannula 504 extends. Spaced inward of second end 507 is wall 508 to which the second end of cutting cannula 504 connects. This connection is such that central bore 511 of cutting cannula 504 is not obstructed.

Cutting cannula 504, as stated, has its second end fixed in elongated connection block 502 at wall 508. First end 510 of cutting cannula 504 is distal to elongated center block 502 and beveled. Central bore 511 has a diameter slightly larger than the outside diameter of needle section 304. This will permit the needle section to slide smoothly within central bore 511 of cutting cannula 504.

Referring to FIGS. 16 and 24, needle assembly 104, as assembled, is shown. FIG. 16 shows how connection block 302 fits into the opening in elongated connection member 502 and needle section 304 fits into bore 511 of cutting cannula 504. In FIG. 24, the relationship between end 312 of needle section 304 and end 510 of cutting cannula 504 is shown. Moreover, in this Figure, the specimen notches are shown in better detail. The size of the tissue specimen is determined by the amount of the specimen notch that is exposed to the tissue of interest. The larger the size of the notch exposed, the larger the tissue specimens. This is controlled by the distance the stylet is advanced into the tissue of interest and any movement of the cutting cannula when it is cocked and fired.

Figure 25:
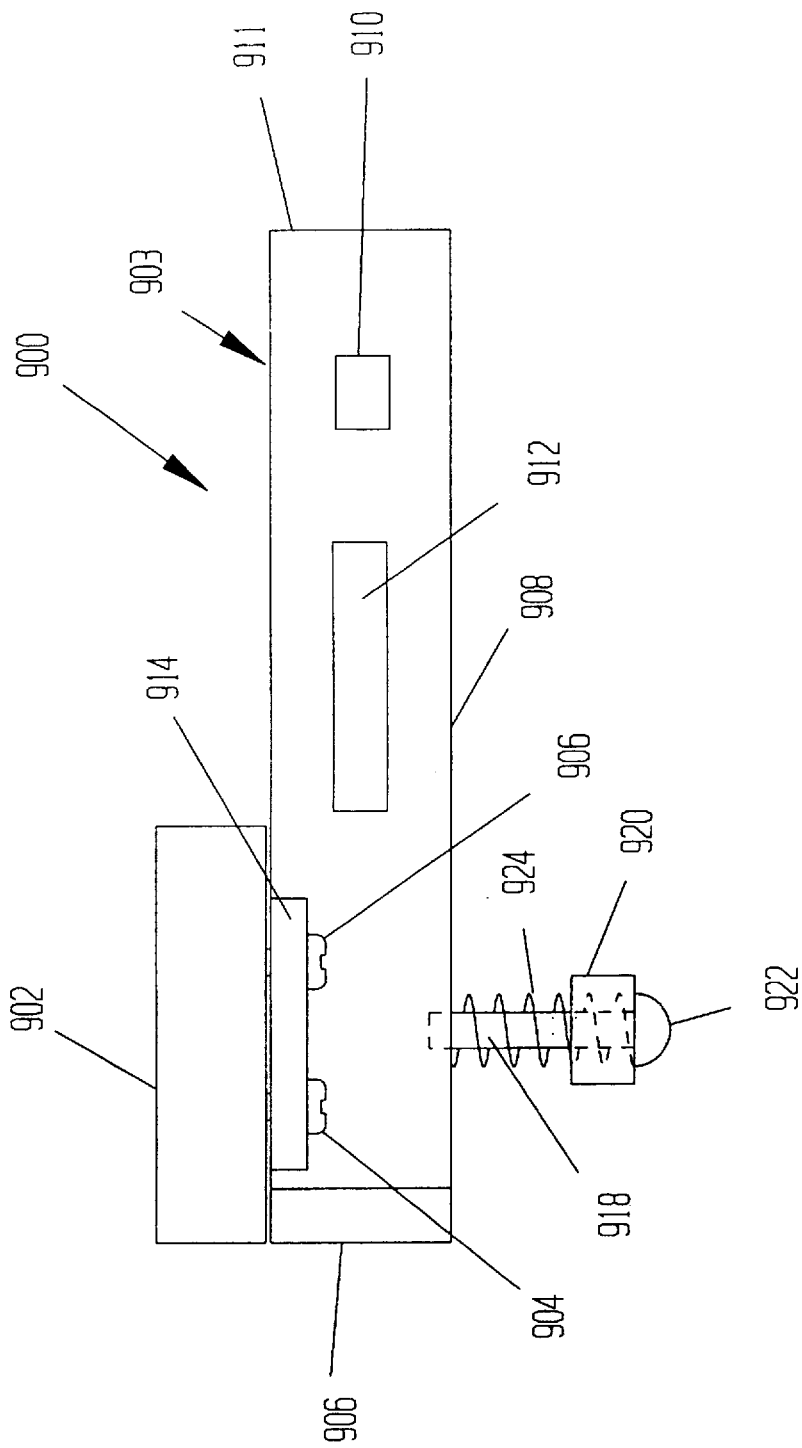
FIG. 25 shows a second embodiment of the carriage assembly of the needle adapter system.

FIG. 25, generally at 900, shows a second embodiment of the cutting cannula carriage assembly of needle adapter system 106. This embodiment includes carriage guide block 902, hollow carriage connector 903, pin 918, biasing spring 924, and pin cap 920 with rounded end 922. Carriage guide block 902, like carriage guide block 242 of the first embodiment of the cutting cannula carriage assembly, has a longitudinal channel (not shown) in the top surface for receiving carriage guide 200. Bearing sets also are disposed between the carriage guide 200 and carriage guide block 902 to permit carriage guide block 902 to move smoothly along carriage guide 200.

Four downwardly disposed pins extend from the bottom surface of carriage guide block 902 in the same fashion as pins 232, 236, 605, and 703 extend from the bottom surface of carriage guide block 242 of the first embodiment of the cutting cannula carriage assembly. In FIG. 25, two of the four pins are shown: pins 904 and 906.

Hollow carriage connector 903 has body 908. This body has two cannula locking members of which only member 910 is shown. Hollow carriage connector 903 has two stop members of which only stop member 912 is shown. The locking members and stop members are similar to those described in the preferred embodiment.

First end 911 of body 908 is rounded and second end 906 has a flange for receiving the first end of cocking spring 214. These elements operate like their counterparts in the first embodiment of cutting cannula carriage assembly of the needle adapter system.

Body 908 has upper plate member 914 which has holes for receiving therethrough the pins disposed from the bottom of carriage guide block 902. However, in this embodiment, the pins connect upper plate member 914 directly to carriage guide block 902 such that body 908 is not vertically movable with respect to carriage guide block 902 as it is in the first embodiment of the cutting cannula carriage assembly.

The bottom of body 908 has pin 918 disposed downwardly from it. Pin 918 has pin cap 920 at its distal. This pin cap has rounded end 922 that contacts the upwardly sloping surface of cocking member 154.

Spring 924 is disposed around pin 918 and has one end in cap 920 and the other against the bottom of body 908. The spring biases pin cap 920 downwardly. The proximal end of pin 918 is connected to body 908 such that pin cap 920 may move upward against biasing spring 924 so that cutting cannula assembly 500 may be cocked and fire.

When the second embodiment of the cutting cannula carriage assembly, shown generally at 900, is used, needle assembly 104 does not move vertically upward when the CSC system of the present invention is cocked and fired. The cutting cannula carriage assembly at 900 is used when it may be disadvantageous to have vertical movement of the needle assembly to obtain tissue specimens. The second embodiment of the cutting cannula carriage assembly provides the same precision advancement of the needle assembly, controlled firing of the cutting cannula assembly to obtain tissue specimens, and one handed operation.

Referring primarily to FIGS. 2–6, the operation of the double trigger CSC system of the present invention will be described. With the double triggers of the CSC biopsy system unengaged, the coincident beveled ends of the cutting cannula 504 and needle section 304 are placed at the position on the patient's body where the insertion is to take place. The physician then moves the entire CSC system forward until the tip of the needle assembly is adjacent the tissue of interest. The physician's index finger now engages upper trigger 130 and rotates it in direction "A." This will cause pinion gear 160 to rotate in the same direction. When the pinion gear rotates in direction "A," teeth 162 of this gear, which mesh with rack members 172 of elongated rack element 170, cause elongated rack element 170 to move in direction "C." Since drive rod 620 of drive cap 210 is disposed in opening 178 of driving end member 177 of elongated rack element 170, a portion of needle adapter system 106 also will be driven in direction "C."

The driving of stylet 300 of needle assembly 104 in direction "C" is caused by elongated rod 212, which is connected to drive cap 210, being driven in direction "C" and this, in turn, drives stylet 300, which is connected to the end of the elongated rod, in direction "C." Cutting cannula 504 of cutting cannula assembly 500 is not driven in direction "C" by drive cap 210 along with stylet 300 because cocking spring 214, which is around elongated rod 212, absorbs the forward movement drive cap 210 caused by the upper trigger. As such, spring 214 does not transmits the driving force from drive cap 210 to hollow carriage connector 218.

When trigger 130 is rotated fully in direction "A", as shown in FIG. 4, stylet 300 extends from within the cutting cannula. The amount that it extends from within the cutting cannula depends on the amount the upper trigger is rotated.

Once upper trigger 130 is rotated a desired amount, lower trigger 142 is engaged with the middle finger and moved in direction "D." As the lower trigger is moved in direction "D," the upwardly sloping top surface of locking pin driver 152 contacts head 186 of locking pin 184 driving locking pin 184 upward. This will result in end 188 of driving locking pin 184 engaging the sawtooth bottom edge of toothed lock member 176. When toothed lock member 176 is so engaged, stylet 300 is locked from further movement in either direction "C" or "D" since there is a hard connection between elongated rack element 170 and stylet 300 via drive rod 620, drive cap 210, and elongated rod 212. This, however, cannot be said for the connection between elongated rack element 170 and cutting cannula assembly 500 because this connection includes cocking spring 214 which is compressible. Thus, drive cap 210 in its fixed position provides a member against which cocking spring 214 may be compressed.

To cock and fire cutting cannula assembly 500, lower trigger 142 is moved in direction "D," as described. As it is moved in this direction, stylet 300 is locked from movement in either direction "C" or "D." The further movement of lower trigger 142 in direction "D," causes ball bearing 226 in receiver 224 to partially ride up the upwardly sloping top surface of cocking member 154. Because the springs around the pins that are disposed downwardly from carriage guide block 242 of cutting cannula carriage assembly 216 bias body 219 downwardly, ball bearing 226 will not ride up the entire upwardly sloping top surface of cocking member 154 until cocking spring 214 is compressed to the point where it can overcome the downward force caused by the pin springs. Until this point is reached, as the lower trigger is moved further in direction "D," hollow carriage connector 218, along with the attached cutting cannula assembly 500 are moved in direction "D."

Once the CSC system of the present invention is cocked to the point where compressed cocking spring 214 can overcome the bias of the springs around the pins disposed downwardly from carriage guide block 242, ball bearing 226 moves up the upwardly sloping top surface of cocking member 154. In doing this, cutting, cannula carriage assembly 216, cutting cannula assembly 500, and stylet 300 (disposed within cutting cannula assembly 500) are moved upwardly which ensures tissue is disposed in one of the specimen notches.

When ball bearing 226 reaches the top end of the upwardly sloping top surface of cocking member 154, cocking spring 214 decompresses, filing cutting cannula carriage assembly 216 in direction "C." This results in cutting cannula 504 being driven back over needle section 304 such that the beveled ends of the two are again aligned as shown in FIG. 24. This action cuts tissue which is trapped in the specimen notches.

Holding the two triggers depressed or releasing them both, the CSC biopsy system is withdrawn from the patient. Once removed, the tissue specimens are recovered and a new needle assembly is attached to needle adapter system 106. The CSC biopsy system now is ready for its next use.

Alternatively, cutting cannula assembly 300 may be disconnected by depressing the stops members. Once this happens, the gun unit, needle adapter system, and stylet may be withdrawn leaving the cutting cannula assembly in place. After the tissue specimen is removed from the specimen notch or notches, the stylet may be reinserted into the cutting cannula assembly, locked into place, and additional tissue specimens may be obtained, for example, at different depths in the tissue of interest. This may be accomplished with only one insertion of the cutting cannula assembly.

Figure 26:
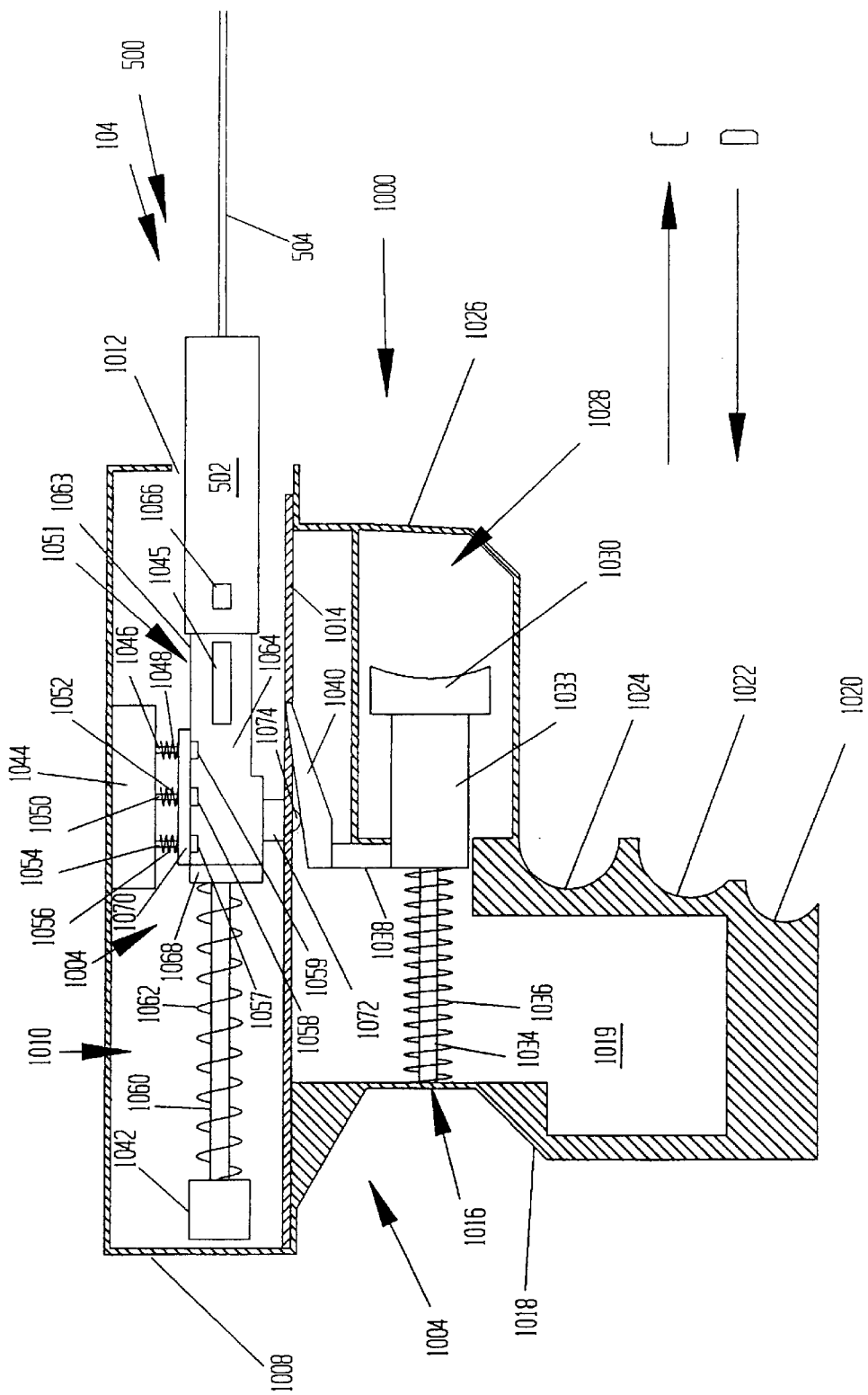
FIG. 26 shows a cross-sectional view of the gun unit of single trigger embodiment of the controlled surgical core biopsy system of the present invention.

FIG. 26, generally at 1000, shows a cross-sectional view of the single trigger embodiment of the CSC biopsy system of the present invention. This second embodiment of the CSC biopsy system does not have a trigger for separately advancing stylet 300 of needle assembly 104 into the tissue of interest. In this embodiment, the needle assembly is advanced into the tissue of interest by the physician moving the entire the CSC biopsy system to place the end of the needle assembly there. Once the needle assembly is properly positioned in the tissue of interest, cutting cannula 504 is cocked and fired over needle section 304 to obtain a tissue sample.

The single trigger CSC biopsy system includes gun unit 1002, needle adapter system 1004, and needle assembly 104. As in the preferred embodiment, needle adapter system 1004 is used to connect needle assembly 104 to gun unit 1002.

Gun unit 1002 includes upper portion 1008, handle body 1016, and trigger guard assembly 1026. Upper portion 1008 includes open area 1010, and has rectangular opening 1012 in a first end and a closed second end. Horizontally disposed flat members 1014, which have a channel between them (like the one between flat members 114 of the preferred embodiment in FIG. 7), form part of the bottom of the upper portion of gun unit 1002. Handle body 1016 has portion 1018 that is meant to fit into the physician's palm, and finger grips 1020, 1022, and 1024 are for the physician's little, ring, and middle fingers, respectively.

Single trigger assembly 1028 rides on guide rod 1034 that extends forward from the rear wall of handle body 1016. Single trigger assembly 1028 includes trigger body 1033 that has trigger head 1030 fixed at a first end and vertical member 1038 disposed upwardly from the second end. Trigger body 1033 has a central bore (not shown) that receives guide rod 1034. This permits single trigger assembly 1028 to move in directions "C" and "D" guided by guide rod 1034.

Vertical member 1038 has cocking member 1040 disposed from the top end. When single trigger assembly 1028 is moved in direction "C," the upwardly sloping top surface of cocking member 154 cocks cutting cannula assembly 500.

Guide rod 1034 has return spring 1036 disposed around it. The first end of return spring 1036 contacts the end of trigger body 1033 and the second end of this spring contacts the inside wall of handle body 1016. Therefore, when the single trigger is engaged and moved in direction "D," return spring 1036 is compressed; however, when the single trigger is no longer engaged, spring 1036 will urge the trigger assembly in direction "C," back to its original position.

Needle adapter system 1004 includes spring cap 1042, elongated rod 1060, cocking spring 1062, and cutting cannula carriage assembly 216. These elements are used to connect needle assembly 104 to gun unit 1002.

Spring cap 1042 is a hollow, cylindrical-shaped member with one open end. Elongated rod 1060 is disposed in the open end of the spring cap that is fixed to the rear wall of the upper portion of the units 102.

The distal end of elongated rod 1060 connects to stylet 300 of needle assembly 104. As in the preferred embodiment, the distal end of elongated rod 1060 is configured with a shape that will mate with needle assembly 104 in a locking relationship.

Cutting cannula carriage assembly 1051 includes carriage block 1044, hollow carriage connector 1063, and six pins that connect the two elements. Carriage block 1044 is connected to the top interior wall of upper gun portion 1008. Carriage block 1044 has six downwardly disposed pins extending from its bottom surface. Three of the six pins are shown in FIG. 26. Each of the pins has a head of sufficient size to prevent it from passing out of the hole in upper plate member 1070 of hollow carriage connector 1063 through which it is disposed. Specifically, pins 1046, 1050, and 1054 are shown, and these pins have heads 1059, 1058, and 1057, respectively. The other three pins are disposed through upper plate member 1070 of hollow carriage connector 1063 on the opposite side of the hollow carriage member in a fashion similar to the way pin 605 is disposed through upper plate 230 (FIG. 7) on the opposite side of body 219 of cutting cannula carriage assembly 216. Although six pins are shown, more or less may be used and still be within the scope of the present invention.

Each pin has a biasing spring disposed between carriage block 1044 and upper plate member 1070. Three of these springs are shown in FIG. 26. Spring 1048 is associated with pin 1046, spring 1052 associated with pin 1050, and spring 1056 associated with pin 1054. These springs, along with the ones associated with the other three pins (not shown), bias hollow carriage connector 1063 downwardly for cocking cutting cannula assembly 500.

Hollow carriage connector 1063 has body 1064 that has a rounded front end similar to the first end 221 of hollow carriage connector 218 of the preferred embodiment. The rounded front end of body 1064 makes it easier to mate hollow carriage connector 1063 with cutting cannula assembly 500. Spaced back from the rounded front end of body 1064 and extending outward from the sides of the body are cannula locking members. FIG. 26 shows cannula locking member 1066. The second cannula locking member that extends outward from the opposite side wall of body 1064 is not shown. The second cannula locking member is similar to cannula locking member 706 of the preferred embodiment. The cannula locking members are used to connect hollow carriage connector 1063 to cutting cannula assembly 500 of needle assembly 104.

Spaced back further from the rounded front end of body 1064 and also extending from the sides of the body are stop members. Only stop member 1065 is shown in FIG. 26. Body 1064, like body 219 of the preferred embodiment, has a second stop member (not shown) that extends outward from the opposite side wall. The two stop members are used to stop the rearward movement of the end of cutting cannula assembly 500 that connects to hollow carriage connector 1063. As in the preferred embodiment, the locking member and stop member for each side of hollow carriage connector 218 are formed from a single piece of material that connects to the body like a leaf spring. When this configuration is used, each leaf spring connects to the body at one location and the locking member and stop member are biased to extend through respective openings in the side wall. This configuration also permits the physician to depress the stop members to connect or disconnect the cutting cannula assembly. This happens because depressing the stop members causes the locking members to retract into body 1064. This arrangement also facilitates front end loading the needle assembly, The bottom of body 1063 has ball bearing receiver 1072 extending down from it. Ball bearing 1074 is inserted in the open end of ball bearing receiver 1072 and freely rotates in the receiver. Ball bearing 1074 contacts the upwardly sloping surface of cocking member 1040 of single trigger assembly 1028.

End 1068 of body 1064 opposite the rounded front end has a flange (not shown) that serves as a stop for cocking spring 1062. The use of this spring will be described in detail subsequently.

When needle adapter system 1051 is properly disposed in gun unit 1002, elongated rod 1060 extends from spring cap 1042 through body 1064 of hollow carriage connector 1063. Spring 1062 is disposed over elongated rod 1060 with a first end fixed to flange 1068 of body 1063 and a second end fixed in spring cap 1042.

The second embodiment of the cutting cannula carriage assembly that is shown in FIG. 25, generally at 900, may be used with the single trigger embodiment of the CSC biopsy system of the present invention.

Referring to FIG. 26, the operation of the single trigger CSC system of the present invention will be described. With the single trigger of the CSC biopsy system unengaged, the coincident beveled ends of the cutting cannula 504 and needle section 304 are placed at the position on the patient's body where the insertion is to be made. The physician will manually insert needle assembly 104 into the tissue of interest. As needle assembly 104 is driven into the patient and into the tissue of interest, the beveled ends of needle section 304 and cutting cannula 504 have the relationship shown in FIG. 24.

To cock and fire cutting cannula assembly 500, single trigger 1030 is moved in direction "D." This will cause ball bearing 1074 in receiver 1072 to ride partially up the upwardly sloping top surface of cocking member 1040. Because the springs around the pins that are disposed downwardly from carriage block 1044 of cutting cannula carriage assembly 1051 bias body 1064 downwardly, ball bearing 1074 will not ride entirely up the upwardly sloping top surface of cocking member 1040 until cocking spring 1060 is compressed to the point where it can force the ball bearing up the upwardly sloping top surface against the springs around the pins. Until this point is reached (as the single trigger is moved in direction "D" , assembly hollow carriage connector 1063, along with the attached cutting cannula assembly 500, will move further in direction "D." As this is done, cutting cannula 504 is drawn back over needle section 304 of stylet 300 exposing opposing specimen notches 306 and 308 to the tissue of interest.

Once the CSC system of the present invention is cocked to the point where compressed cocking spring 1062 can overcome the bias of the springs around the pins disposed downwardly from carriage block 1044, ball bearing 1074 moves up the upwardly sloping top surface of cocking member 1040. In doing this, cutting cannula carriage assembly 1051, cutting cannula assembly 500, and stylet 300 (disposed within cutting cannula assembly 500) are moved upwardly which ensures tissue is disposed in one of the specimen notches.

When ball bearing 1074 reaches the top end of the upwardly sloping top surface of cocking member 1040, cocking spring 1060 decompresses, firing cutting cannula carriage assembly 1051 and cutting cannula assembly 500 in direction "C." As the firing takes place, cutting cannula 504 is fired back over needle section 304 so that the beveled ends of the two are again aligned as shown in FIG. 24. This action also cuts the tissue that is trapped in the specimen notches.

Now, the CSC biopsy system is withdrawn from the patient and the needle assembly is removed. The tissue specimens are recovered, and a new needle assembly is attached to needle adapter system 106. The single trigger CSC biopsy system is again ready for use.

As discussed with respect to the preferred embodiment, once the tissue specimen is trapped, the cutting cannula assembly may be disconnected so that stylet 300 may be withdrawn to remove the tissue specimen from the specimen notch or notches. After this is done, the stylet may be reinserted into the cutting cannula assembly to obtained more tissue specimens. Thus, a number of tissue specimens may be obtained with one insertion of the cutting cannula assembly.

Figure 27:
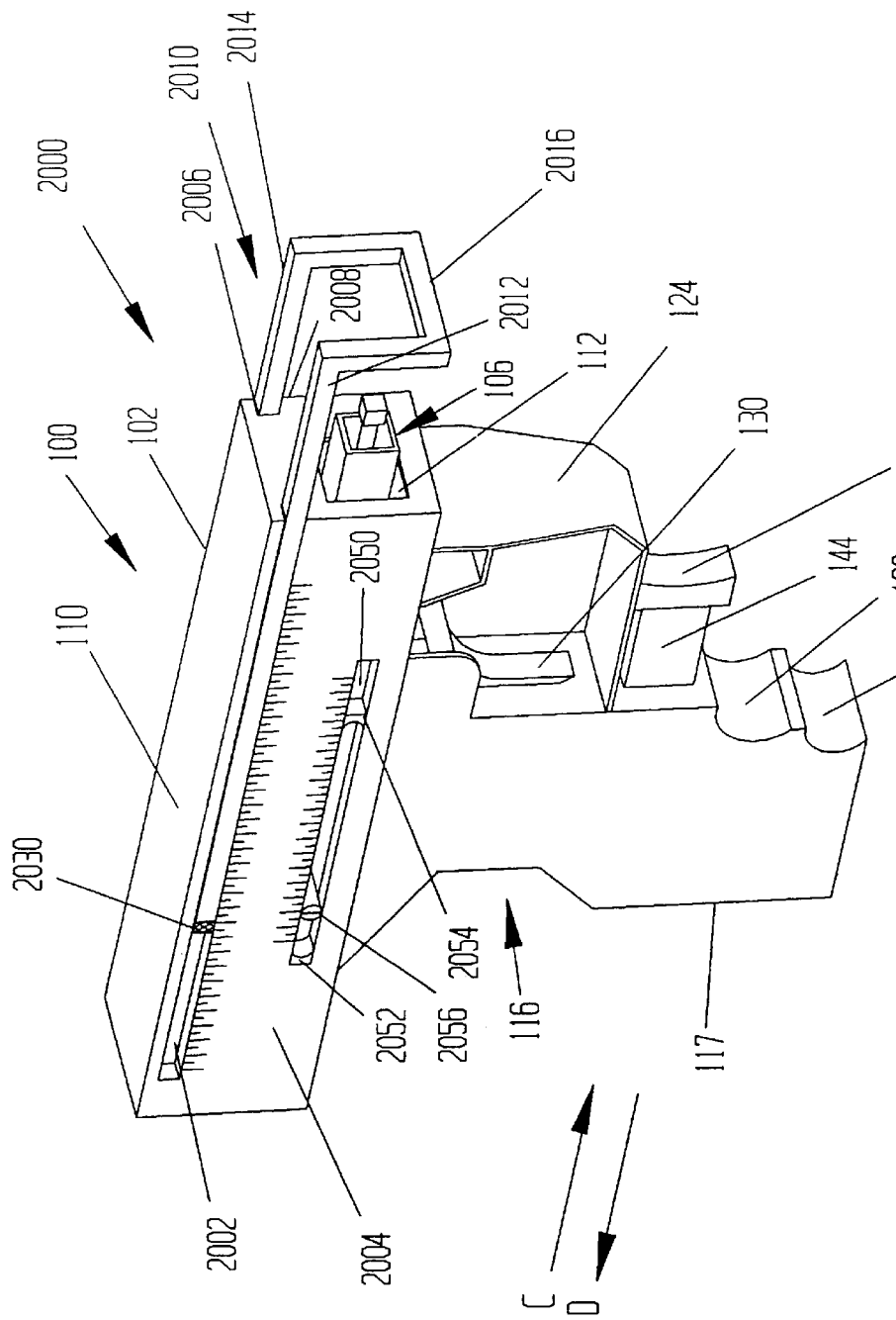
FIG. 27 shows another embodiment of the controlled surgical core biopsy system of the present invention that includes a slide member for more accurately determining at least the depth the needle assembly is inserted.

FIG. 27, generally at 2000, shows a third embodiment of the CSC biopsy system of the present invention. In this embodiment, the internal and external structures are substantially the same as the that for the double trigger embodiment shown in FIGS. 1–24 except that it at least includes a slide member for more accurately determining the depth the needle assembly is inserted in the patient. In describing the embodiment of the CSC biopsy system shown in FIG. 27, the elements that are the same as those in the double trigger embodiment shown in FIGS. 1–24 will have the same reference numbers. Further, since the elements and operation of this third embodiment of the present invention is substantially the same as double trigger embodiment shown in FIGS. 1–24, the description of the elements and operation of the double trigger embodiment are incorporated by reference. The additional novel features of the third embodiment of the present invention shown in FIG. 27 will now be discussed.

Referring to FIG. 27, upper portion 110 of housing 102 has longitudinally extending slide groove 2002 in side wall 2004 and longitudinally extending slide groove 2006 in side wall 2008. Each slide groove is near the top of the side wall in which it is disposed.

Slide member 2010 includes slide segments 2012 and 2014, and U-shaped end member 2016 that connects the two slide segments. Slide segment 2012 is disposed in longitudinally extending slide groove 2002 and slide segment 2014 is disposed in longitudinally extending slide groove 2006. Slide member 2010 is movable in directions "C" and "D" in the slide grooves.

Side walls 2004 and 2008 below longitudinally extending slide grooves 2004 and 2006, respectively, have calibration marks to show the position of U-shaped end member 2016 with respect to upper portion 110 of housing 102. A stop, such as stop 2030 in longitudinally extending slide groove 2002, is disposed in each of the longitudinally extending grooves for controlling the maximum depth that needle assembly may be manually inserted into the patient. As the needle assembly is being inserted, its progressive depth is indicated by the position of the ends of the slide segments along the scale below each of the longitudinally extending slide grooves.

In operation, needle assembly 104 is attached to needle adapter system 106. Slide end member 2016 is pulled out until it is even with the end of the needle assembly. As the needle assembly is inserted into the patient, slide segments 2012 and 2014 move indirection "D" in slide grooves 2002 and 2006, respectively. This is continued until the ends of the slide segments either reach a desired depth or the ends of the slide segments contact the stops disposed in the respective slide grooves.

The slide grooves and slide member also may be used with the single trigger embodiment shown in FIG. 26. When they are used with this embodiment, they operate as described for the third embodiment of the CSC biopsy system of the present invention.

Upper portion 110 of housing 102 also has elongated, rectangular opening 2050 through side wall 2004 below longitudinally extending slide groove 2002. Rectangular opening 2050 has fixed rear stop 2052 disposed at the rear end and stop 2054 that is movable in directions "C" and "D" within the open Drive cap 210 (FIG. 2) has rod 2056 extending radially outward from the wall. Rod 2056 extends into elongated, rectangular opening 2050. The distal end of rod 2056 has a vertical line disposed on it to indicate the position of the rod with respect to the scale disposed above elongated, rectangular opening 2050.

Stops 2052 and 2054, along with rod 2056, control the distance that upper trigger 130 can drive stylet 300 of needle assembly 104 into the tissue of interest after the needle assembly is placed adjacent to such tissue.

In operation, before needle assembly 106 is inserted into the patient, stop 2054 is set to the desired position in elongated, rectangular opening 2050. Once needle assembly 106 is inserted and adjacent the tissue of interest, rod 2056 is against rear stop 2052. As upper trigger 130 is rotated, rod 2056 moves in direction "C" in elongated, rectangular opening 2050. When the rod reaches movable stop 2054, the forward movement of stylet 300 is stopped. This method allows for inserting the end of the stylet a precise distance into the tissue of interest.

The terms and expressions that are employed herein are terms or description and not of limitation. There is no intention in the use of such terms and expressions of excluding the equivalents of the feature shown or described, or portions thereof, it being recognized that various modifications are possible within the scope of the invention as claimed.

I claim:

1. A needle assembly for front loading to a biopsy sampling system, comprising:

an outer needle structure further comprising, a first sleeve member for slideably receiving a shaped member of an inner needle structure, the first sleeve member having a first end and a second end, the first end of the first sleeve member having a connector for connecting the first sleeve to the biopsy sampling system, the first end of the first sleeve member forming the proximal end of the outer needle structure, a second sleeve member for slideably receiving an elongated needle of an inner needle structure, with the second sleeve member having a proximal end connected to that the second end of the first sleeve member and a distal end of the second sleeve member forming a distal end of the outer needle structure; and the inner needle structure further comprising, a shaped member with a connection structure formed therein, the shaped member forming a proximal end of the inner needle structure, with the shaped member being capable of being located in at least a first position near the first end of the first sleeve member and a second position closer to the second end of the first sleeve member, an elongated needle having a proximal end extending from a second end of the shaped member, the elongated needle having at least one tissue receiving member disposed near a distal end, the distal end of the elongated needle forming the distal end of the inner needle structure, with the distal end and tissue receiving member of the elongated needle extending from the distal end of the second sleeve member when the shaped member is in at least the second position and the distal end and tissue receiving member of the elongated needle being retracted within the second sleeve member when the shaped member is in at least the first position.

2. The needle assembly as recited in claim 1, wherein the first sleeve member is hollow with the first end open and the second end closed.

3. The needle assembly as recited in claim 1, wherein second sleeve member is hollow and the distal end is beveled.

4. The needle assembly as recited in claim 1, wherein outside cross-sectional dimensions of the shaped member are less than inside cross-sectional dimensions of the first sleeve member.

5. The needle assembly as recited in claim 1, wherein outside cross-sectional dimensions of the elongated needle is less than inside cross-sectional dimensions of the second sleeve member.

6. The needle assembly as recite d in claim 1, wherein the elongated needle has a plurality of tissue receiving members.

7. The needle assembly as recited in claim 1, wherein the distal end of the elongated needle is beveled.

8. The needle assembly as recited in claim 3, wherein the distal end of the elongated needle is beveled at an angle substantially the same as the angle of bevel at the distal end of the second sleeve member.

9. The needle assembly as recited in claim 1, wherein the connector of the first sleeve member detachably connects the first sleeve member to a first structure of the biopsy sampling system.

10. The needle assembly as recited in claim 9, wherein the connection structure of the shaped member detachably connects the shaped member to a second structure of the biopsy sampling system for moving the shaped member to at least the first and second positions.

* * * * *